US006723548B2

(12) United States Patent
Lloyd et al.

(10) Patent No.: US 6,723,548 B2
(45) Date of Patent: Apr. 20, 2004

(54) DNA REPAIR POLYPEPTIDES AND METHODS OF USE

(75) Inventors: R. Stephen Lloyd, Galveston, TX (US); Amanda K. McCullough, Galveston, TX (US); Khoa Nguyen, Galveston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/864,866

(22) Filed: May 23, 2001

(65) Prior Publication Data

US 2002/0127656 A1 Sep. 12, 2002

Related U.S. Application Data

(60) Provisional application No. 60/206,279, filed on May 23, 2000.

(51) Int. Cl.$^7$ .............................. C12N 9/26; C12N 9/88; C01D 15/08; C12D 21/08; C07K 16/00
(52) U.S. Cl. .................. 435/200; 435/232; 435/455; 424/94.61; 530/387.3; 530/388.21
(58) Field of Search ............... 435/200, 232, 435/455; 424/94.61; 530/387.3, 388.21

(56) References Cited

U.S. PATENT DOCUMENTS

| | | | |
|---|---|---|---|
| 4,794,075 A | 12/1988 | Ford et al. | |
| 5,190,762 A | 3/1993 | Yarosh | |
| 5,302,389 A | 4/1994 | Kripke et al. | |
| 5,994,095 A | 11/1999 | Kamb | |
| 6,017,706 A | 1/2000 | Parshad et al. | |
| 6,103,746 A | 8/2000 | Yarosh | |

FOREIGN PATENT DOCUMENTS

WO    WO 97/31612 A    9/1997

OTHER PUBLICATIONS

Nilsen H. et al., Nuclear and mitochondrial uracil–DNA glycosylases are generated by alternative splicing and transcription from different positions in the UNG gene, Nucleic Acids research, 1997, 25, 750–755.*
Lu Z. et al., Analysis of 45 kb of DNA located at the end of the chlorella virus PBCV–1 genome, Virology (1995), 206, 339–352.*
Valerie K. et al. Identification physical map location and sequence of the denV gene from bacteriophage T4, Nucleic Acid Res. 1984, 12/21, 8085–8096.*
Piersen C. E. et al. Purification and cloning of *Micrococcus luteus* ultraviolet endonuclease, and N–glycosylase/abasic lyase that proceeds via an imino enzyme–DNA intermediate, J. Biol. Chem. 1995, 270/40, 23475–23484.*
Ananthaswamy et al., "Molecular mechanisms of ultraviolet radiation carcinogenesis," *Photochem Photobiol*. Dec. 1990;52(6):1119–36.

Ausubel et al., (Eds.) Current Protocols in Molecular Biology, John Wiley & Sons, Inc. New York, NY. (1994).
Ballinger et al., "Hydrogen peroxide causes significant mitochondrial DNA damage in human RPE cells," *Exp. Eye Res*. Jun. 1999;68(6):765–72.
Ballinger et al., "Hydrogen peroxide– and peroxynitrite–induced mitochondrial DNA damage and dysfunction in vascular endothelial and smooth muscle cells," *Circ Res*. May 12, 2000;86(9):960–6.
Ballinger et al., "Mitochondrial genome damage associated with cigarette smoking," *Cancer Res*. Dec. 15, 1996;56(24):5692–7.
Benhamou et al., "Variability in nucleotide excision repair and cancer risk: a review," *Mutat Res*. Apr. 2000;462(2–3):149–58. Review.
Bohr et al., "DNA repair in an active gene: removal of pyrimidine dimers from the DHFR gene of CHO cells is much more efficient than in the genome overall," *Cell*. Feb. 1985;40(2):359–69.
Chong et al., "Single–column purification of free recombinant proteins using a self–cleavable affinity tag derived from a protein splicing element," *Gene*, Jun. 19, 1997;192(2):271–81.
Clarkson et al., "The use of an immunological probe to measure the kinetics of DNA repair in normal and UV–sensitive mammalian cell lines," *Mutant Res*. Oct. 1983;112(5):287–99.
Cleaver, J., "Common pathways for ultraviolet skin carcinogenesis in the repair and replication defective groups of xeroderma pigmentosum," *J Dermatol Sci*. May 2000;23(1):1–11.
Furuta et al., "Chlorella virus PBCV–1 encodes a homolog of the bacteriophage T4 UV damage repair gene denV," *Appl Environ Microbiol*. Apr. 1997;63(4):1551–6.
Garvish et al., "Active–site determination of a pyrimidine dimer glycosylase," *J Mol Biol*. Jan. 21, 2000;295(3):479–88.
Garvish et al., "The catalytic mechanism of a pyrimidine dimer–specific glycosylase (pdg)/abasic lyase, Chlorella virus–pdg," *J Biol Chem*. Apr. 2, 1999;274(14):9786–94.

(List continued on next page.)

Primary Examiner—Rebecca Prouty
Assistant Examiner—Malgorzata A. Walicka
(74) Attorney, Agent, or Firm—Mueting, Raasch & Gebhardt, P.A.

(57) ABSTRACT

The present invention provides polypeptides having pyrimidine glycosylase activity, preferably, pyrimidine glycosylase/AP lyase activity. The polypeptides include a targeting sequence, preferably an exogenous target sequence. The invention includes polynucleotides that include a coding sequence encoding the polypeptides of the present invention. Also provided by the invention are methods of using the polypeptides.

7 Claims, 10 Drawing Sheets

OTHER PUBLICATIONS

Genbank Accession No. AF128160 National Center for Biotechnology Information, National Library of Medicine, National Institutes of Health, GenBank Locus AF128160, Accession No. AF128160, "Chlorella virus isolate PBCV–1 pyrimidine dimer–specific glycosylase gene, complete cds," [online]. Bethesda, MD [retrieved on May 21, 2001]. Retrieved from the Internet:<URL: http://www.ncbi.nlm.nih.gov/entrez/query.fcgi?cmd=Retrieve&db=nucleotide&list_uids=4927992&dopt=GenBank, 2 pages.

Genbank Accession No. X04567 National Center for Biotechnology Information, National Library of Medicine, National Institutes of Health, GenBank Locus MYT4ER1, Accession No. X04567 J02514 M24240 V00860 X01124, "Bacteriophage T4 DNA for 58.3 to 65.5 kb early region," [online]. Bethesda, MD [retrieved on May 21, 2001]. Retrieved from the Internet:<URL: http://www.ncbi.nlm.nih.gov/entrez/query.fcgi?cmd=Retrieved&db=nucleotide&list_uids=15260&dopt=GenBank, 10 pages.

Genbank Accession No. U22181, National Center for Biotechnology Information, National Library of Medicine, National Institute of Health, GenBank Locus MLU22181, Accession No. U22181, "*Micrococcus luteus* ultraviolet N–glycosylase/AP lyase gene, complete eds."[online]. Bethesda, MD retrieved on May 21, 2001. Retrieved from the Internet:<URL: http://www.ncbi.nlm.nih.gov/entrez/query.fcgi?cmd=Retrieve&db=nucleotide&li st_uids=726272&dopt=GenBank, 2 pages.

Horwich et al., "Structure and expression of a complementary DNA for the nuclear coded precursor of human mitochondrial ornithine transcarbamylase," *Science*, Jun. 8, 1984;224(4653):1068–74.

Jorgensen et al., "Identification and characterization of human mitochondrial tryptophanyl–tRNA synthetase," *J Biol Chem*. Jun. 2, 2000;275(22): 16820–6.

Kim, J.–S. et al., "Ribonuclease S–peptide as a carrier in fusion proteins," *Protein Sci*. Mar. 1993;2(3):348–56.

Kripke, "Ultraviolet radiation and immunology: something new under the sun—presidential address," *Cancer Res*. Dec. 1, 1994;54(23):6102–5.

Lloyd, "Base excision repair of cyclobutane pyrimidine dimers," *Mutat Res*. Sep. 11, 1998;408(3):159–70.

Lloyd, "The initiation of DNA base excision repair of dipyrimidine photoproducts," *Prog Nucleic Acid Res Mol Biol*. 1999;62:15–75.

Lloyd, "T4 Endonuclease V—Structure/Function Analyses," Grant Abstract, Grant No. 5R01ES004091–13 [online], National Institute of Environmental Health Sciences, project dates Jul. 01, 1992–May 31, 2001 [retrieved on Nov. 20, 2001]. Retrieved from the Internet: URL: http://commons.cit.nih.gov/crisp3/crisp_lib.getdoc?textkey= 6077934&p_grant_n um=5R01ES004091—13&p_ query=& ticket=139233&p_audit_session_id=160203 9&p_keywords=, 2 pages.

McCullough et al., "Initiation of base excision repair: glycosylase mechanisms and structures," *Annu Rev Biochem*. 1999;68:255–85.

McCullough et al., "Characterization of a novel cis–syn and trans–syn–II pyrimidine dimer glycosylase/AP lyase from a eukaryotic algal virus, Paramecium bursaria chlorella virus–1," *J Biol Chem*. May 22, 1998;273(21):13136–42.

Mitchell et al., "Repair of pyrimidine(6–4)pyrimidone photoproducts in mouse skin," *J Invest Dermatol*. Jul. 1990;95(1):55–9.

Moroianu, "Nuclear import and export pathways," *J Cell Biochem*. 1999;Suppl 32–33:76–83.

Nishigori et al., "Evidence that DNA damage triggers interleukin 10 cytokine production in UV–irradiated murine keratinocytes," *Proc Natl Acad Sci U S A*, Sep. 17, 1996;93(19):10354–9.

O'Neill et al, "A quantitative assay of mutation induction at the hypoxanthine–guanine phosphoribosyl transferase locus in Chinese hamster ovary cells (CHO/HGPRT system): utilization with a variety of mutagenic agents," *Mutant Res*. Oct. 1977;45(1):103–9.

Otterlei et al., "Nuclear and mitochondrial splice forms of human uracil–DNA glycosylase contain a complex nuclear localisation signal and a strong classical mitochondrial localisation signal, respectively," *Nucleic Acids Res*. Oct. 15, 1998;26(20):4611–7.

Patrick, In: Photochemistry and Photobiology of Nucleic Acids, Wang (ed.) vol. II, Academic Press, New York, pp. 1–32 (1976)).

Sambrook et al, Molecular Cloning: A Laboratory Manual., Cold Srping Harbor Laboratory Press (1989).

Sarasin, "The molecular pathways of ultraviolet–induced carcinogenesis," *Mutat Res*. Jul. 16, 1999;428(1–2):5–10.

Tatusova, et al., "BLAST 2 Sequences, a new tool for comparing protein and nucleotide sequences," *FEMS Microbiol Lett*. May 15, 1999;174(2):247–50.

Ullrich et al, "Sunscreen effects on UV–induced immune suppression," *J Investig Dermatol Symp Proc*. Sep. 1999;4(1):65–9.

Watanabe et al., "The roles of the C–terminal domain and type III domains of chitinase A1 from *Bacillus circulans* WL–12 in chitin degradation," *J Bacteriol*. Aug. 1994;176(15):4465–72.

Wikonkal et al., "Ulraviolet radiation induced signature mutations in photocarcinogenesis," *J Investig Dermatol Symp Proc*. Sep. 1999;4(1):6–10.

Wispe et al., "Synthesis and processing of the precursor for human mangano–superoxide dismutase," *Biochim Biophys Acta*. Jan. 19, 1989;994(1):30–6.

Wolf et al., "Sunscreens and T4N5 liposomes differ in their ability to protect against ultraviolet–induced sunburn cell formation, alterations of dendritic epidermal cells, and local suppression of contact hypersensitivity," *J Invest Dermatol*. Feb. 1995;104(2):287–92.

Yang et al., "Prevention of apoptosis by Bcl–2: release of cytochrome o from mitochondria blocked," *Science*. Feb. 21, 1997;275(5303):1129–32.

Yarosh et al., "Photoprotection by topical DNA repair enzymes: molecular correlates of clinical studies," *Photochem Photobiol*, Feb. 1999;69(2):136–40.

Yoon et al., "The DNA damage specrum produced by simulated sunlight," *J Mol Biol*. Jun. 9, 2000;299(3):681–93.

Ziegler et al., "Tumor suppressor gene mutations and photocarcinogenesis," *Photochem Photobiol*. Apr. 1996;63(4):432–5.

Hilbert et al., "Purification of a Mammalian Homologue of *Escherichia coli* Endonuclease III: Identification of a Bovine Pyrimidine Hydrate–Thymine Glycol DNA–Glycosylase/ AP Lyase by Irreversible Cross Linking to a Thymine Glycol–Containing Oligodeoxynucleotide," *Biochemistry*, 35(8):2505–2511 (1996).

Pearl et al., "DNA repair in three dimensions," *TIBS Trends In Biochemical Sciences, Elsevier Publication*, 20(10): 421–426 (1995).

Swanson et al., "Overlapping Specificities of Base Excision Repair, Nucleotide Excision Repair, Recombination, and Translesion Synthesis Pathways of DNA Base Damage in *Saccharomyces cerevisiae*", *Molecular and Cellular Biology*, 19(4):2929–2935 (1999).

* cited by examiner

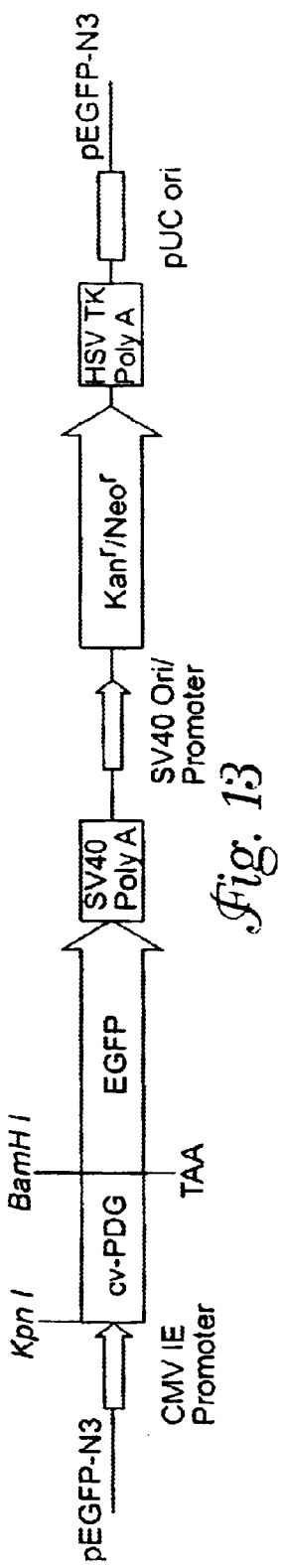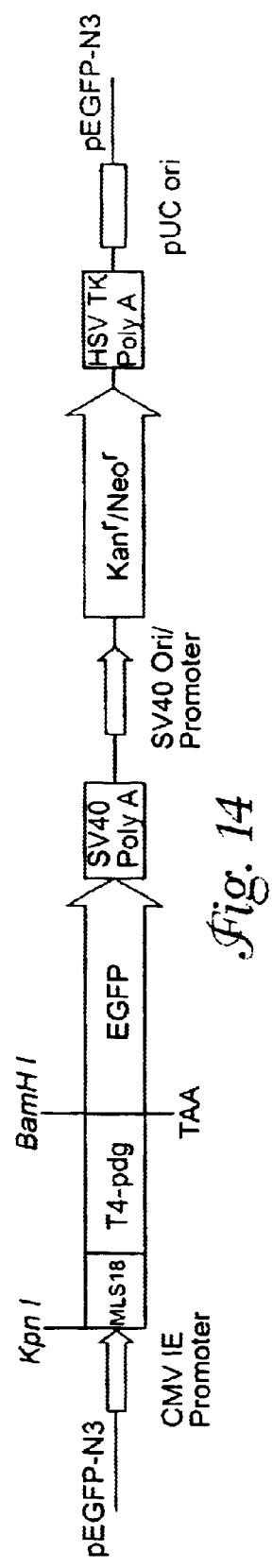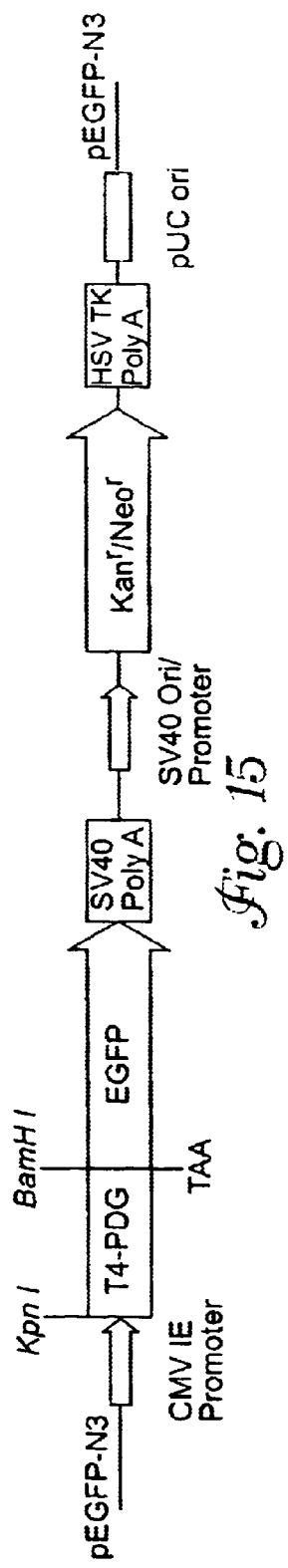

SEQ ID NO:41;
MTRVLVFNGELADQHLMGEFRELKVIPGALARSLRTQSSEKLKKPSKFTLIITGHVLFFTDKGKVLGGRDEVVELVEGVKMNEAPLFDKVVGEKWNDYT
PTEDAFRIIPARIAEKIAMKPSFVRFTKAKTSNN

SEQ ID NO:42;
MTRIRLILSELADGHLMGETRELEFVFGAVRHVAUGPVEDFKISPTFLLGAGHVTFFTDKEPJPVKGVELIAEGLKPGHIPTTVKGISPIFEFFGCVIPH
EASIAISQARLDEKIAQRPTWIKTIGKAIVA

SEQ ID NO:43;
METESTGTPTGETRLALVPEARFIDRILAETYPVAVAELDFETPFELLVATYLSAGTTDVFMAATPALFARPFPAHANAAATEPELQELVPSTGFVRNKASAILRL
SGEVGRHGSEVFARLEDLVALPGVSKKTAFVVLGNAFGQPGITVDTHFGRLAPFLGFTDETDPGKGRAPFGRPWPFAPDWTNLSHRLIFHGRPVCHARPAGRPCP
LARWCPSYAAGETDPERARALLAYELKPGREELLELLRAGRTAGAAGPRPRAGG

Fig. 24

SEQ ID NO:44;

```
  1 atgacacgtg tgaatctcgt accggttcaa gaattagctg accagcatct catgccagaa
 61 tttcgtgaac ttaagatgat tcgcaaggca ctcgcaagaa gttttcgaac tcaatcgtcc
121 gaaaaatat tgaagaagat cccatcaaaa ttactctga acactggtca tgtttctgtt
181 tttacgata aaggcaagta tttgcaacaa cgatacgacg aaattgtcgt tgaacttgtt
241 gatagggggt ataagataaa cgttgacgct aaattcgacc ctgataacgt gatgacggga
301 gagtggtaca atgattacac cccaacagaa gatcgtttta atattattcg agcgaggatt
361 gccgaaaaaa tcgcctatga accaagtttt tacaggttca cgaaagctaa aaccagcaat
421 aattaa
```

SEQ ID NO:45;

```
  1 atgactcgta tcaaccttac tttagtatct gaattggctg accaacactt aatggctgaa
 61 tatctgtaat tgccgcgtgt ttttggtgca gttcgtaagc atgttgctaa cggtaaaacgt
121 gttcgtgatt ttaaaatcag tcctactttt atccttggcg caggtcatgt tacattcttt
181 tacgataagc tcgagttctt acgtaaaacgt caaattgagc ttatagctga atgtttaaaa
241 cgtgttttta atatcaagga tactacagtc caggatatta gtgatatttc tcaggaattc
301 cgtgtgatt atattccca tgaagttct attgctatat cacaagctcg tttagatgaa
361 aaaattgcac aacgtcctac ttggtacaaa tactacggta aggcgattta tgcataa
```

SEQ ID NO:46;

```
  1 atgcgcccgg aagcggggc cggacccggt gtggacgtcg catgcgcccc gtccctagg
 61 atggtcggac ctgagcggat cgcacgggga cggaggaca cgcggatgga gacgagtcg
121 acgggcacgc cgaccgggga gaccccggct gcccctggtgc ggccggcgcg gcggatcgac
181 cggatcctgg ccgagacgta cccgtacgcc gtcgccgagc tggacttcga gacgccgttc
241 gagctgtcg tggccacggt ctgccgcc cagaccaccg acgtgcggt caacgaagcc
301 acgccgcgc tgttcgcccg gctccccgat gccacgcga tgccgcggc caccgagccc
361 gagctgcagg agcgctgcg aggagctgcg cgcacacggg ttctaccgga acaaggcctc ccgcgatccg
421 cggctgtccc aggagctcgt tgccggcac gacggcgagg tcccgaggac cttcgaggac
481 ctcgtggcgc tgcccgggt tgcccgggt acgcgtcg tggtgctgg caaggccttc
541 ggccagcccg ggatcaccg ggacacgcgt gcacgcgcac tcggccggc tggggttc
601 acggacgaga cggactctc taaaggtcga atcttccacg gccgccgcgt tccccgggcg
661 cgggactgga cgatgctctc ccaccggctg atcttccacg gcgcccggac gtgccacgcg
721 cgcgccggg cgtgcggcg gtgcccgatc gtgccgatc gcccggcga gcccgcggg
781 gagaccgacc ccgcggggc gcgcgcccg ctggcctacg cgggctacg agctcaagcc cgccgcggg
841 gagctgctcg agctcctgcg agcctgcg ctggccgag acggggag ctggcggag cggcacggg
901 gctggagcgt gccgccgg ctgccccgct cagccttttc ggtgagaccc ggtgagatcgc
961 gaccgccg
```

DNA REPAIR POLYPEPTIDES AND METHODS OF USE

CONTINUING APPLICATION DATA

This application claims the benefit of U.S. Provisional Application Ser. No. 60/206,279, filed May 23, 2000, which is incorporated by reference herein.

GOVERNMENT FUNDING

The present invention was made with government support under Grant No. ES04091, awarded by the National Institutes of Health. The Government has certain rights in this invention.

BACKGROUND

DNA damage caused by ultraviolet (UV) light can lead to mutations, carcinogenesis, and cell death (Ananthaswamy and Pierceall, *Photochem. Photobiol.*, 52, 1119–1136 (1990), Ziegler et al., *Photochem. Photobiol.*, 63, 432–435 (1996)). UV-induced DNA damage occurs frequently in DNA as the bases of nucleic acids absorb light in a range coincident with that of natural sunlight, making the bases susceptible to photochemically induced alterations (Patrick, In: *Photochemistry and Photobiology of Nucleic Acids*, Wang (ed.) Vol. II, Academic Press, New York, pp. 1–32 (1976)).

Ultraviolet (UV) light is the principle cause of basal and squamous cell carcinomas and possibly melanomas. UV light can also lead to mutations and cell death (Ananthaswamy and Pierceall, *Photochem. Photobiol.*, 52, 1119–1136 (1990), Ziegler et al., *Photochem. Photobiol.*, 63, 432–435 (1996)). The vast majority of nonmelanoma skin cancers occur on portions of the body that are chronically exposed to sun. Additionally, molecular analyses of DNA sequences of oncogenes in skin tumor cells often reveals a signature tandem UV-induced mutations of CC to TT (Wikonkal and Brash, *J. Investig. Dermatol. Symp. Proc.*, 4, 6–10 (1999)). This tandem mutation is strongly indicative of cis-syn cyclobutane pyrimidine dimers and (6–4) photoproducts, two types of photoproducts produced by exposure of DNA to sunlight.

Following exposure to UV light, humans undergo a temporary, reversible immunosuppression (Kripke *Cancer Res.*, 54, 6102–6105 (1994), Ullrich et al, *J. Investig. Dermatol Symp Proc.*, 4, 65–69 (1999)). Recent data suggest that the molecular trigger for this signal transduction cascade is the persistence of the damaged DNA itself (Nishigori et al., *Proc. Natl. Acad. Sci., U.S.A.*, 93, 10354–10359 (1996), and Wolf et al., *J. Invest. Dermatol.*, 104, 287–92 (1995)).

The human DNA repair system that is responsible for the removal of these DNA lesions is the nucleotide excision repair (NER) pathway, which removes a patch of damaged DNA by incising the damage-containing DNA strand both 5' and 3' to the damage (Cleaver, *J. Dermatol Sci.*, 23, 1–11 (2000), and Sarasin, *Mutat. Res.*, 428, 5–10 (1999)). Polymerases and helicases act in conjunction to remove the patch and resynthesize new, undamaged DNA. A DNA ligase then completes repair by sealing the remaining break (reviewed in Benhamou and Sarasin, *Mutat. Res.*, 462, 149–158 (2000)).

In contrast to the NER pathway, human cells have the capacity to avoid the consequences of replicating damaged DNA by moving the damaged strand through homologous recombination opposite an undamaged DNA. This mechanism does not remove damage, but gives the cell additional time to excise the lesion without being forced to replicate potentially mutagenic DNA.

Human cells also have an additional pathway for removing many types of DNA lesions, including cis-syn cyclobutane pyrimidine dimers, that arise from UV light, oxidative stress, alkylation damage and deamination, among others. This pathway is termed the base excision repair (BER) system, and although it removes many lesions, in humans there are no enzymes that initiate repair at sites of UV induced damage. The first step in this pathway involves the recognition and removal of the damaged base by a class of enzymes called glycosylases. These enzymes break the glycosyl bond and a subset of these enzymes also possesses the ability to incise the phosphodiester backbone through a lyase reaction. Downstream of these reactions, the pathway requires the activities of an abasic (AP) site endonuclease, DNA polymerase(s) and DNA ligase. Thus in humans, the pathway is intact and robust, but concerning the repair of UV-induced damage, the first enzyme is missing.

Glycosylases exist that can initiate repair at sites of UV induced damage. The T4-pdg enzyme (also referred to as endonuclease V), produced by the denV gene of the bacteriophage T4, catalyzes the rate limiting, first step in the removal of UV-induced DNA damage, namely, single strand incision of DNA at the site of damage. Other glycosylases having the ability to repair DNA damage have also been identified, and include the *Micrococcus luteus* ultraviolet N-glycosylase/AP lyase and the *Paramecium bursaria chlorella* Virus-1 PBCV-1 pyrimidine dimer-specific glycosylase.

SUMMARY OF THE INVENTION

The present invention represents an advance in the art of repairing DNA lesions that result from, for instance, UV light, oxidative stress, alkylation damage and/or deamination. The introduction to human cells of a glycosylase having the appropriate initiating repair activity would result in cells possessing a fully functional BER pathway. The implications of this would be a faster, more efficient repair of potentially mutagenic and carcinogenic damage. Another benefit would be that this enhanced rate of repair would help to prevent immunosuppression caused by DNA damage. T4-pdg, the glycosylase/AP lyase that can initiate repair at sites of UV induced damage, has been delivered to human cells to increase the repair of damaged DNA; however, the enzyme has not been targeted to the cellular organelles containing the DNA to be repaired, i.e., the nucleus and the mitochondria of a cell. In the present invention, amino acid sequences that promote intracellular nuclear and mitochondrial targeting have been added to enzymes that initiate repair in the BER system.

The present invention provides a polypeptide having pyrimidine glycosylase activity, preferably, pyrimidine glycosylase/AP lyase activity. The polypeptide includes a targeting sequence, preferably an exogenous target sequence. The invention includes a composition that contains the polypeptide and a pharmaceutically acceptable carrier.

In some aspects of the present invention, the polypeptide includes an amino acid sequence of SEQ ID NO:41, SEQ ID NO:42, or SEQ ID NO:43 and a targeting sequence, preferably an exogenous targeting sequence. In other aspects of the present invention, the polypeptide includes an amino acid sequence having pyrimidine glycosylase/AP lyase activity and having at least about 15% identity with an amino acid sequence of SEQ ID NO:41, SEQ ID NO:42, or SEQ ID NO:43, and a targeting sequence, preferably an exogenous targeting sequence.

The present invention is further directed to a polynucleotide that includes a coding sequence encoding a polypeptide having pyrimidine glycosylase activity, preferably pyrimidine glycosylase/AP lyase activity. The polypeptide includes a targeting sequence, preferably, an exogenous targeting sequence.

In some aspects of the present invention, the polynucleotide includes a coding sequence encoding a polypeptide having pyrimidine glycosylase/AP lyase activity and a targeting sequence, preferably, an exogenous coding sequence. The polynucleotide includes a nucleotide sequence of SEQ ID NO:44, SEQ ID NO:45, or SEQ ID NO:46. In other aspects of the present invention, the polynucleotide includes a coding sequence encoding a polypeptide having pyrimidine glycosylase/AP lyase activity and including a targeting sequence, preferably, an exogenous coding sequence. The polynucleotide includes a nucleotide sequence having at least about 10% identity with a nucleotide sequence of SEQ ID NO:44, SEQ ID NO:45, or SEQ ID NO:46.

The present invention provides a method for increasing the repair rate of damaged bases in a cell. The method includes introducing to a cell exposed to or at risk of exposure to an agent that damages DNA a composition that includes an amount of a polypeptide effective to increase the repair rate of damaged DNA in the cell compared to a cell that does not include the polypeptide. The polypeptide has pyrimidine glycosylase activity, preferably pyrimidine glycosylase/AP lyase activity, and includes a targeting sequence, preferably, an exogenous targeting sequence.

Also provided is a method for treating mutagenesis in a subject. The method includes introducing to a subject exposed to or at risk of exposure to an agent that damages DNA a composition that includes an effective amount of a polypeptide having pyrimidine glycosylase activity, preferably pyrimidine glycosylase/AP lyase activity, and includes a targeting sequence, preferably, an exogenous targeting sequence.

The present invention provides a method for treating immunosuppression in a subject. The method includes introducing to a subject exposed to or at risk of exposure to an agent that damages DNA a composition that includes an effective amount of a polypeptide having pyrimidine glycosylase activity, preferably pyrimidine glycosylase/AP lyase activity, and includes a targeting sequence, preferably, an exogenous targeting sequence.

Further provided by the present invention is a method for treating tumor formation in a subject. The method includes introducing to a subject exposed to or at risk of exposure to an agent that damages DNA a composition that includes an effective amount of a polypeptide having pyrimidine glycosylase activity, preferably pyrimidine glycosylase/AP lyase activity, and includes a targeting sequence, preferably, an exogenous targeting sequence.

The present invention also provides a method for treating apoptotic cell formation in a subject. The method includes introducing to a subject exposed to or at risk of exposure to an agent that damages DNA a composition that includes an effective amount of a polypeptide having pyrimidine glycosylase activity, preferably pyrimidine glycosylase/AP lyase activity, and includes a targeting sequence, preferably, an exogenous targeting sequence.

Unless otherwise specified, "a," "an," "the," and "at least one" are used interchangeably and mean one or more than one.

BRIEF DESCRIPTION OF THE FIGURES

FIG. 13. Plasmid cv-pdg-x-pEGFP-N3 (control, unfused cv-pdg expressed off of CMVIE promoter not fused with EGFP).

FIG. 14. Plasmid MLS18-T4-pdg-x-pEGFP-N3 (In frame fusion of MLS18 with T4-pdg with a stop codon between T4-pdg and EGFP).

FIG. 15. Plasmid T4-pdg-x-pEGFP-N3 (control, unfused T4-pdg expressed off of CMVIE promoter, not fused to EGFP).

FIG. 24. Amino acid sequence of Chlorella virus isolate PBCV-1 pyrimidine dimer-specific glycosylase (cv-pdg, Genbank Accession No. AF128160, SEQ ID NO:41), Bacteriophage T4 pyrimidine dimer-specific glycosylase (T4-pdg, Genbank Accession No. X04567, SEQ ID NO:42), and *Micrococcus luteus* ultraviolet N-glycosylase/AP lyase (Mlu-pdg I, Genbank Accession No. U22181, SEQ ID NO:43).

FIG. 25. Nucleotide sequence encoding the Chlorella virus isolate PBCV-1 pyrimidine dimer-specific glycosylase (cv-pdg, Genbank Accession No. AF128160, SEQ ID NO:44), Bacteriophage T4 pyrimidine dimer-specific glycosylase (T4-pdg, nucleotides 1777 to 2193 of Genbank Accession No. X04567, SEQ ID NO:45), and *Micrococcus luteus* ultraviolet N-glycosylase/AP lyase (Mlu-pdg I, nucleotides 106–912 of Genbank Accession No. U22181, SEQ ID NO:46).

DETAILED DESCRIPTION OF PREFERRED EMBODIMENTS OF THE INVENTION

Figure 1:
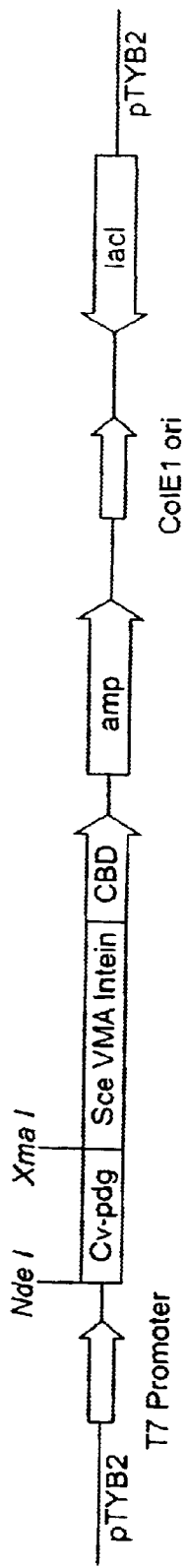
FIG. 1. Plasmid cv-pdg-pTYB2 (In frame fusion of cv-pdg, intein and chitin binding domain).

The present invention provides polypeptides that have pyrimidine glycosylase activity and a targeting sequence, preferably an exogenous targeting sequence. As used herein, "polypeptide" refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like. As used herein, "pyrimidine glycosylase" refers to a polypeptide that recognizes the presence of two consecutive damaged bases in a polynucleotide and catalyzes the breakage of the glycosyl bond between the 5' base and the DNA sugar-phosphate backbone. A polypeptide that recognizes the presence of two consecutive damaged pyrimidine bases and catalyzes the breakage of such a bond has "glycosylase activity." Whether a polypeptide has pyrimidine glycosylase activity can be determined by measuring the ability of the polypeptide to cleave the glycosyl bond of the 5' pyrimidine of a cyclobutane pyrimidine dimer in DNA. Such methods are known to the art. A polypeptide having pyrimidine glycosylase activity is often referred to in the art as a pyrimidine dimer-specific DNA glycosylase.

As used herein, "polynucleotide" refers to a polymeric form of nucleotides of any length, either ribonucleotides or deoxynucleotides, and includes both double- and single-stranded DNA and RNA. A polynucleotide may include nucleotide sequences having different functions, including, for instance, coding sequences, and non-coding sequences such as regulatory sequences. Coding sequence, non-coding sequence, and regulatory sequence are defined below. A polynucleotide can be obtained directly from a natural source, or can be prepared with the aid of recombinant, enzymatic, or chemical techniques. A polynucleotide can be linear or circular in topology. For example, a polynucleotide can be a portion of a vector, such as an expression or cloning vector, or a fragment.

As used herein, "damaged base" and "damaged bases" refers to structural deviations in nucleoside-5'-monophosphates present in a eukaryotic cell's genomic DNA. One type of structural deviation is a covalent joining of the adjacent pyrimidines through the formation of a cyclobutane ring structure at the C5 and C6 positions. Another type of structural deviation is an imidazole ring fragmentation of a purine (either adenine or guanine). The location of such structural deviations in a cell's genomic DNA is referred to as a "lesion." As used herein, "genomic DNA" refers to the DNA present in the nucleus and the mitochondria of a cell. Damaged bases preferably arise from, for instance, UV radiation, ionizing radiation, oxidative stress, alkylation damage, and deamination. Examples of lesions include cis-syn and trans-syn II cyclobutane pyrimidine dimers, FapyA and FapyG (Lloyd, *Mutat. Res.*, 408, 159–170 ((1998), and Lloyd, *Progress in Nucleic Acid Research and Molecular Biology*, 62, 155–175 (1999)).

Optionally and preferably, a polypeptide of the present invention also has apurinic/apyrimidinic lyase activity (AP lyase activity). A polypeptide having pyrimidine glycosylase activity and AP lyase activity is referred to herein as a "pyrimidine glycosylase/AP lyase," and has "pyrimidine glycosylase/AP lyase activity." Thus, a preferred polypeptide of the present invention has pyrimidine glycosylase/AP lyase activity and a targeting sequence, preferably an exogenous targeting sequence. As used herein, "AP lyase activity" refers to the ability of a polypeptide to catalyze a β-elimination reaction on an abasic site containing DNA, resulting in an α, β unsaturated aldehyde. A polypeptide having pyrimidine glycosylase/AP lyase activity is often referred to in the art as a "pyrimidine dimer specific DNA glycosylase/AP lyase."

Whether a polypeptide has pyrimidine glycosylase/AP lyase activity can be determined by measuring the ability of the polypeptide to incise a target polynucleotide containing damaged bases in the presence of a buffer. The target polynucleotide contains damaged bases, preferably, UV radiation induced pyrimidine dimers. An example of a target polynucleotide is disclosed in the Examples. Preferably, the target polynucleotide is present at a concentration of from about 0.1 nM to about 10 nM. The putative glycosylase/AP lyase is present at a concentration of from about 0.01 nM to about 100 nM. Buffers in which a glycosylase/AP lyase is active are suitable for the assay. Preferably, the buffer includes about 25 mM $NaH_2PO_4$. Preferably, the pH is from about 6.5 to about 7.5, more preferably about 6.8. Preferably the buffer contains from about 10 mM NaCl to about 125 mM NaCl, more preferably about 100 mM NaCl. Preferably the buffer contains from about 1 mM EDTA to about 10 mM EDTA, more preferably about 1 mM EDTA. Preferably the buffer contains from about 0.01 mg/mL bovine serum albumin (BSA) to about 1 mg/mL BSA, more preferably about 0.1 mg/mL BSA. Preferably, the temperature of the assay is about 37° C. The assay can be carried out for at least about 10 seconds to no greater than about 8 hours. Preferably, the assay is about 30 minutes. A polypeptide having pyrimidine glycosylase/AP lyase activity will cause the mobility of the target polynucleotide to change relative to the polynucleotide that has not been exposed to the polypeptide. The polypeptide may be present in a crude cellular extract, preferably isolated, more preferably, purified. Since polypeptides identified in this assay as having pyrimidine glycosylase/AP lyase activity function on UV-irradiated DNAs, these polypeptides identify cyclobutane pyrimidine dimers, and are likely to be active on other UV-induced photoproducts including FapyA and Fapy G.

Individual microbes, preferably *Neisseria mucosa* and *Bacillus sphearicus*, and viruses can be screened for the ability to produce polypeptides that have pyrimidine glycosylase activity, preferably pyrimidine glycosylase/AP lyase activity. As used herein, "microbe" refers to prokaryotic organisms. The production by a microbe, or a microbe harboring a virus, of a polypeptide having pyrimidine glycosylase activity, preferably pyrimidine glycosylase/AP lyase activity, can be assayed by, for instance, the ability of the microorganism to incise a target polynucleotide containing damaged bases.

Preferred examples of polypeptides having pyrimidine glycosylase activity include amino acid sequences present in the Chlorella virus isolate PBCV-1 pyrimidine dimer-specific glycosylase (cv-pdg, polypeptide sequence available at Genbank Accession No. AF128160, SEQ ID NO:41), the Bacteriophage T4 pyrimidine dimer-specific glycosylase (T4-pdg, polypeptide sequence available at Genbank Accession No. X04567, SEQ ID NO:42), and the *Micrococcus luteus* ultraviolet N-glycosylase/AP lyase (Mlu-pdg I, polypeptide sequence available at Genbank Accession No. U22181, SEQ ID NO:43). Preferably, a polypeptide having pyrimidine glycosylase activity includes amino acid sequences present in cv-pdg (SEQ ID NO:41) or T4-pdg (SEQ ID NO:42).

The present invention further includes polypeptides having pyrimidine glycosylase activity, preferably pyrimidine glycosylase/AP lyase activity, and amino acid identity with the amino acid sequence of SEQ ID NO:41, SEQ ID NO:42, or SEQ ID NO:43, preferably SEQ ID NO:41 or SEQ ID NO:42. Amino acid identity is defined in the context of a comparison between a polypeptide and SEQ ID NO:41 or SEQ ID NO:42, and is determined by aligning the residues of the two amino acid sequences (i.e., a candidate amino acid sequence and the amino acid sequence of SEQ ID NO:41, SEQ ID NO:42, or SEQ ID NO:43) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in SEQ ID NO:41, SEQ ID NO:42, or SEQ ID NO:43. A candidate amino acid sequence can be isolated from a microbe or a microbe harboring a virus, or can be produced using recombinant techniques, or chemically or enzymatically synthesized. Preferably, two amino acid sequences (i.e., the candidate amino acid sequence and the amino acid sequence present in SEQ ID NO:41, SEQ ID NO:42, or SEQ ID NO:43) are compared using the Blastp program of the BLAST 2 search algorithm, as described by Tatusova, et al. (*FEMS Microbiol Lett* 1999, 174:247–250), and available at www.ncbi.nlm.nih.gov/gorf/bl2.html. Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, amino acid identity is referred to as "identities." Preferably, a polypeptide having pyrimidine glycolase activity has an amino acid sequence having, in increasing order of preference, at least about 15% amino acid identity, at least about 30% amino acid identity, at least about 40% amino acid identity, at least about 50% amino acid identity, and most preferably, at least about 60% amino acid identity to SEQ ID NO:41, SEQ ID NO:42, or SEQ ID NO:43.

The polypeptides useful in some aspects of the invention include an active analog or active fragment of SEQ ID NO:41, SEQ ID NO:42, or SEQ ID NO:43. An active analog or active fragment of a pyrimidine glycosylase is one having pyrimidine glycosylase activity, preferably pyrimidine glycosylase/AP lyase activity. Active analogs of a pyrimidine glycosylase include polypeptides having amino acid substitutions that do not eliminate the ability to incise a target polynucleotide containing damaged bases. Substitutes for an amino acid may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, aspartate, and glutamate. The positively charged (basic) amino acids include arginine, lysine, and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Active analogs, as that term is used herein, also include modified polypeptides. Modifications of polypeptides of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Active fragments of a polypeptide include a portion of the polypeptide containing deletions or additions of one or more contiguous or noncontiguous amino acids such that the resulting polypeptide will incise a target polynucleotide containing damaged bases.

The polypeptides of the present invention also include a targeting sequence, preferably, an exogenous targeting sequence. As used herein, a "targeting sequence" is a polypeptide that is fused to a polypeptide having pyrimidine glycosylase activity, preferably pyrimidine glycosylase/AP lyase activity. As used herein, "exogenous targeting sequence" refers to a foreign targeting sequence, i.e., a targeting sequence that is not normally fused to the polypeptide having pyrimidine glycosylase activity, preferably, pyrimidine glycosylase/AP lyase activity. Targeting sequences cause the polypeptide to which they are fused to migrate from the cytoplasm of a cell to an organelle. In one aspect, the targeting sequence is a nuclear localization sequence (NLS) that causes migration into the nucleus. During the transit of the polypeptide that includes an NLS to the nucleus of a cell, the NLS may be cleaved. The invention is not limited by the type of NLS that is fused to the pyrimidine glycosylase, and many NLSs are known to the art (see, for instance, (Moroianu, *J. Cell. Biochem. Suppl.* 32/33, 76–83 (1999)). An NLS can be present in any location in a polypeptide of the present invention provided the presence of the NLS does not inhibit the pyrimidine glycosylase activity of the polypeptide after the pyrimidine glycosylase is delivered to the nucleus. Preferably, an NLS is present at the carboxy terminal end of a pyrimidine glycosylase. The amino acid sequences of preferred examples of NLSs that can be used in the present invention include a consensus NLS, PKKRKRRL (SEQ ID NO:27) and PKKKRKRL (SEQ ID NO:30).

In another aspect, the targeting sequence is a mitochondria localization sequence (MLS) that causes migration into mitochondria. The invention is not limited by the type of MLS that is fused to the pyrimidine glycosylase. Typically, an MLS is present fused to the amino terminal end of a polypeptide of the present invention. In those aspects of the invention where an MLS is fused to the amino terminal end of a pyrimidine glycosylase, the MLS is cleaved during the transit of the polypeptide that includes the MLS into a cell's mitochondria. In some aspects, the pyrimidine glycosylase, preferably pyrimidine glycosylase/AP lyase, of the present invention are inactive while the MLS is fused, but are active after the MLS is cleaved upon transit into a mitochondrion. Examples of MLSs that can be used include those present in polypeptides that are targeted to the mitochondria, including, for instance, mitochondrial tryphtophanyl-tRNA synthetases (Jorgensen et al., *J. Biol. Chem.*, 275, 16820–16826 (2000)), mitochondrial uracil DNA glycosylase (Otterlei et al., *Nucleic Acids Research,* 26, 4611–4617 (1998)), manganese superoxide dismutase (Wispe et al., Biochim Biophys Acta, 994, 30–36 (1989)), and ornithine transcarbamylase (Horwich et al., Science 224, 1068–1074 (1984)), among others. Preferred examples of MLSs that can be used in the present invention include MALHSMRKARERWSFIRA (SEQ ID NO:1) and MGVFCLGFWGLGRKLRTFGKGPKQLLSRLCGDHLQ (SEQ ID NO:47).

Whether a polypeptide of the present invention is delivered to the appropriate organelle can be determined by several methods. The polypeptide can be introduced to a eukaryotic cell by, for instance, microinjection of the polypeptide into the cytoplasm of the cell. Alternatively and preferably, the polypeptide is introduced to the cytoplasm of the cell as a composition including the polypeptide and a pharmaceutically acceptable carrier, preferably a liposome, phospholipid, or pH-activated lipid. Pharmaceutically acceptable carriers are described herein. To determine whether the introduced polypeptide is targeted to the nucleus or the mitochodria of a cell, the appropriate organelle can be isolated, and the amount of the polypeptide in the organelle determined. Alternatively and preferably, immunofluorescence analysis with antibody that binds to the polypeptide can be used to determine the intracellular distribution of the polypeptide after it is introduced.

When determining whether a polypeptide of the invention is delivered to the appropriate organelle, the polypeptide may be introduced to the cell as a polynucleotide encoding the polypeptide. The polypeptide is expressed from the polynucleotide and translated in the cytoplasm of the cell. The targeting of the polypeptide to the nucleus or mitochondria of a cell can be determined as described above. It should be noted that as used herein, a polynucleotide encoding the polypeptide is used ex vivo to test whether a polypeptide is delivered to the nucleus or a mitochondrion; polynucleotides are not used for the in vivo delivery of polypeptides of the present invention. Polynucleotides are described herein.

Whether the polypeptide of the present invention retains pyrimidine glycosylase activity, preferably pyrimidine glycosylase/AP lyase activity, once transported into the organelle can be determined by several methods. The polypeptide can be introduced to the cell as described herein, including introduction as a polypeptide and introduction as a polynucleotide that encodes the polypeptide. To measure activity after introduction to the cell, the appropriate organelle can be isolated, the polypeptide isolated from the organelle, and the activity of the isolated polypeptide determined. Alternatively, the repair rate of damaged DNA in the cell can be determined using, for instance, coding sequence-specific repair assays, photoproduct removal, and/or quantitative PCR.

Optionally, a polypeptide of the present invention further includes a series of consecutive amino acids encoding a domain that facilitates the isolation, preferably purification, of the polypeptide. An "isolated" polypeptide or polynucleotide means a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptide or polynucleotide and associated cellular products or other impurities. For instance, domains that are useful in the isolation of a polypeptide that has glycosylase activity, preferably glycosylase/AP lyase activity, include a histidine domain (which can be isolated using nickel-chelating resins), an S-peptide domain (which can be isolated using an S-protein, see Kim, J.-S. et al. Protein Sci 1993 2:348–356), and a chitin binding domain (which can bind to chitin beads, see Chong et al. Gene, 192, 271–281 (1997) and Watanabe et al. J. Bacteriol., 176, 4465–4472 (1994)). Preferably, the domain is present at the carboxy terminal end of the polypeptide. Preferably, the domain can be cleaved from the remainder of the polypeptide (e.g., the polypeptide having pyrimidine glycosylase activity, preferably pyrimidine glycosylase/AP lyase activity, fused to a targeting sequence, preferably an exogenous targeting sequence) by the use of a protease or self-cleaving sequence.

The present invention also provides polynucleotides encoding a polypeptide of the present invention, i.e., a polypeptide having pyrimidine glycosylase activity, preferably, pyrimidine glycosyalse/AP lyase activity, and a targeting sequence, preferably, an exogenous targeting sequence. A polynucleotide may include nucleotide sequences having different functions, including for instance coding sequences, and non-coding sequences such as regulatory sequences. "Coding sequence" and "coding region" are used interchangeably and refer to a polynucleotide that encodes a polypeptide and, when placed under the control of appropriate regulatory sequences expresses the encoded polypeptide. The boundaries of a coding region are generally determined by a translation start codon at its 5' end and a translation stop codon at its 3' end. A regulatory sequence is a nucleotide sequence that regulates expression of a coding region to which it is operably linked. Nonlimiting examples of regulatory sequences include promoters, transcription initiation sites, translation start sites, translation stop sites, and terminators. "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

Polynucleotides encoding a polypeptide of the invention may be obtained from a microbe, preferably Neisseria mucosa and Bacillus sphearicus, or a microbe harboring a virus that produces a polypeptide having pyrimidine glycosylase activity, preferably, pyrimidine glycosylase/AP lyase activity. Methods for isolating a polynucleotide encoding a polypeptide of the invention employs standard cloning techniques known to the art (see, e.g., Sambrook et al, Molecular Cloning: A Laboratory Manual., Cold Spring Harbor Laboratory Press (1989) or Ausubel et al., (Eds.) Current Protocols in Molecular Biology, John Wiley & Sons, Inc. New York, N.Y. (1994)).

Preferred examples of polynucleotides include those encoding the Chlorella virus isolate PBCV-1 pyrimidine dimer-specific glycosylase (cv-pdg, nucleotide sequence available at Genbank Accession No. AF128160, SEQ ID NO:44), the Bacteriophage T4 pyrimidine dimer-specific glycosylase (T4-pdg, nucleotides 1777–2193 of Genbank Accession No. X04567, SEQ ID NO:45), and the Micrococcus luteus ultraviolet N-glycosylase/AP lyase (Mlu-pdg I, nucleotides 106–912 of Genbank Accession No. U22181, SEQ ID NO:46). Preferably, a polynucleotide encoding a polypeptide having pyrimidine glycosylase activity includes the nucleotide sequences encoding cv-pdg (SEQ ID NO:44) or T4-pdg (SEQ ID NO:45).

The present invention further includes polynucleotides encoding polypeptides having pyrimidine glycosylase activity, preferably pyrimidine glycosylase/AP lyase activity, and nucleotide identity with the nucleotide sequence of SEQ ID NO:44, SEQ ID NO:45, or SEQ ID NO:46, preferably, SEQ ID NO:44 SEQ ID NO:45. Nucleotide identity is defined in the context of a comparison between a polypeptide and SEQ ID NO:44, SEQ ID NO:45, or SEQ ID NO:46, and is determined by aligning the residues of the two polynucleotides (i.e., the nucleotide sequence of the candidate coding region and the nucleotide sequence of the coding region of SEQ ID NO:44, SEQ ID NO:45, or SEQ ID NO:46) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate coding region is the coding region being compared to a coding region present in SEQ ID NO:44, SEQ ID NO:45, or SEQ ID NO:46. A candidate nucleotide sequence can be isolated from a microbe or a microbe harboring a virus, or can be produced using recombinant techniques, or chemically or enzymatically synthesized. Preferably, two nucleotide sequences are compared using the Blastn program of the BLAST 2 search algorithm, as described by Tatusova, et al. (*FEMS Microbiol Lett* 1999, 174:247–250), and available at www.ncbi.nlm.nih.gov/gorf/bl2.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. In the comparison of two nucleotide sequences using the BLAST search algorithm, structural similarity is referred to as "identities." Preferably, a polynucleotide includes a nucleotide sequence having a structural similarity with the coding region of SEQ ID NO:44, SEQ ID NO:45, or SEQ ID NO:46 of, in increasing order of preference, at least about 10% identity, at least about 30%, at least about 40% identity, at least about 50% identity, at least about 60% identity, most preferably, at least about 70% identity.

Once a coding region having identity to the coding region present in SEQ ID NO:44, SEQ ID NO:45, or SEQ ID NO:46, preferably, SEQ ID NO:44 or SEQ ID NO:45, has been identified, the coding region can be isolated and ligated into a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, *Molecular Cloning: A Laboratory Manual.*, Cold Spring Harbor Laboratory Press (1989) or Ausubel et al., (Eds.) *Current Protocols in Molecular Biology*, John Wiley & Sons, Inc. New York, N.Y. (1994). A vector can provide for further cloning (amplification of the polynucleotide), i.e., a cloning vector, or for expression of the polypeptide encoded by the coding region, i.e., an expression vector. A vector containing a coding region having identity to the coding region present in SEQ ID NO:44, SEQ ID NO:45, or SEQ ID NO:46 can be conveniently used to insert the nucleotides encoding a targeting sequence, and optionally, a domain that facilitates the isolation of the encoded polypeptide, in frame with the nucleotides encoding the polypeptide having pyrimidine glycosylase activity, preferably, pyrimidine glycosylase/AP lyase activity. Examples of nucleotides encoding an NLS include CCAAAGAAGAGGAAAAG-GAGGCTA (SEQ ID NO:48) and CCAAAGAAAAAGAG-GAAGAGGCTA (SEQ ID NO:49). Examples of nucleotides encoding an MLS include

```
ATGGCGTTACATAGCATGCGCAAAGCGCGCGAACGCTGGAGCTTTATT    (SEQ ID NO: 33)
AGAGCA and ATGGCGTGTTTTGCTTAGGCCCGTGGGGCTTAGGCCGCAAATTACGC    (SEQ ID NO: 34)
ACCCCGGGCAAAGGCCCGTTACAGTTATTATCGCGCTTATGCGGCGAT
CATTTACAG.
```

The term vector includes, but is not limited to, plasmid vectors, viral vectors, cosmid vectors, or artificial chromosome vectors. Typically, a vector is capable of replication in a bacterial host, for instance *E. coli*, or in a eukaryotic cell. Preferably the vector is a plasmid.

Selection of a vector depends upon a variety of desired characteristics in the resulting construct, such as a selection marker, vector replication rate, and the like. Suitable host cells for cloning or expressing the vectors herein are prokaryotic or eukaryotic cells. Preferably the host cell secretes minimal amounts of proteolytic enzymes. Suitable prokaryotes include eubacteria, such as gram-negative or gram-positive organisms, for example, *E. coli*.

An expression vector optionally includes regulatory sequences operably linked to the coding region. The invention is not limited by the use of any particular promoter, and a wide variety are known. Promoters act as regulatory signals that bind RNA polymerase in a cell to initiate transcription of a downstream (3' direction) coding region. The promoter used in the invention can be a constitutive or an inducible promoter. It can be, but need not be, heterologous with respect to the host cell.

Promoter sequences are known for eukaryotes. Most eukaryotic coding regions have an AT-rich region located approximately 25 to 30 bases upstream from the site where transcription is initiated. Another sequence found 70 to 80 bases upstream from the start of transcription of many coding sequences is the CXCAAT region where X may be any nucleotide. At the 3' end of most eukaryotic coding sequences is an AATAAA sequence that may be a signal for addition of the poly A tail to the 3' end of the coding sequence. All these sequences are suitably inserted into eukaryotic expression vectors. The promoter that is normally operably linked to a coding region encoding an polypeptide of the present invention can also be used.

An expression vector can optionally include a ribosome binding site (a Shine Dalgarno site for prokaryotic systems or a Kozak site for eukaryotic systems) and a start site (e.g., the codon ATG) to initiate translation of the transcribed message to produce the enzyme. It can also include a termination sequence to end translation. A termination sequence is typically a codon for which there exists no corresponding aminoacetyl-tRNA, thus ending polypeptide synthesis. The polynucleotide used to transform the host cell can optionally further include a transcription termination sequence. The rrnB terminators, which is a stretch of DNA that contains two terminators, T1 and T2, is an often used terminator that is incorporated into bacterial expression systems. Transcription termination sequences in vectors for eukaryotic cells typically include a polyadenylation signal 3' of the coding region.

Also useful are expression vectors that provide for transient expression in eukaryotic cells of a coding sequence encoding a polypeptide of the invention. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, including a suitable expression vector and a host cell, allow for the convenient positive identification of polypeptides that are targeted to the appropriate organelle. Methods for the transient expression of coding regions are well known in the art.

The polynucleotide used to transform the host cell optionally includes one or more marker sequences, which typically encode a molecule that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, tetracycline, and neomycin.

The compositions of the present invention optionally further include a pharmaceutically acceptable carrier. Typically, the composition includes a pharmaceutically acceptable carrier when the composition is used as described below in "Methods of Use." The compositions of the present invention may be formulated in pharmaceutical preparations in a variety of forms adapted to the chosen route of administration. Formulations include those suitable for topical administration, parental administration (for instance intramuscular, intraperitoneal, or intravenous), oral, transdermal, nasal, or aerosol, preferably, topical. Dosages of the compositions of the invention are typically from about 0.01 mg/kg up to about 0.10 mg/kg.

The formulations may be conveniently presented in unit dosage form and may be prepared by methods well known in the art of pharmacy. All methods of preparing a pharmaceutical composition include the step of bringing the active compound (e.g., a polypeptide of the present invention) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

Typically, the compositions of the invention will be administered as needed, typically at least once per day. The amount of active ingredient that may be combined with the carrier materials to produce a single dosage form will vary depending upon the subject treated and the particular mode of administration. A typical preparation will contain from about 5% to about 95% active compound (w/w). Preferably, such preparations contain from about 20% to about 80% active compound. The amount of active compound in such therapeutically useful compositions is such that the dosage level will be effective to prevent or suppress the condition the subject has or is at risk for. Such conditions are described hereinbelow.

Preferably, a formulation includes a compound that delivers the active compound to the interior of cells, preferably to the interior of living skin cells under the skin's stratum corneum. Accordingly, such compounds deliver the active compounds across the stratum corneum and then across the outer cellular membrane of living cells. Examples of such compounds include liposomes, phospholipids, and pH-activated lipids (see, for example, U.S. Pat. No. 5,190, 762 (Yarosh)).

Formulations suitable for topical administration may include dusting powders, ointments, cremes, gels or sprays for the administration of the active compound to cells, preferably skin cells. Such formulations may optionally include an inorganic pigment, organic pigment, inorganic powder, organic powder, hydrocarbon, silicone, ester, triglyceride, lanolin, wax, cere, animal or vegetable oil, surfactant, polyhydric alcohol, sugar, vitamin, amino acid, antioxidant, free radical scavenger, ultraviolet light blocker, sunscreen agents, preservative, fragrance, thickener, or combinations thereof.

In a particularly preferred embodiment for topical administration, the active compounds of the present invention can be used in cosmetic formulations (e.g., skincare cream, sunscreen, decorative make-up products, and other dermatological compositions) in various pharmaceutical dosage forms, and especially in the form of oil-in-water or water-in-oil emulsions, solutions, gels, or vesicular dispersions. The cosmetic formulations may take the form of a cream which can be applied either to the face or to the scalp and hair, as well as to the human body, in particular those portions of the body that are chronically exposed to sun. They can also serve as a base for a lipstick.

Particularly preferred cosmetic formulations can also include additives such as are usually used in such formulations, for example preservatives, bactericides, perfumes, antifoams, dyes, pigments which have a coloring action, surfactants, thickeners, suspending agents, fillers, moisturizers and/or humectants, fats, oils, waxes or other customary constituents of a cosmetic formulation, such as alcohols, polyols, polymers, foam stabilizers, electrolytes, organic solvents, or silicone derivatives.

Cosmetic formulations typically include a lipid phase and often an aqueous phase. The lipid phase can advantageously be chosen from the following group of substances: mineral oils, mineral waxes oils, such as triglycerides of capric or of caprylic acid, but preferably castor oil; fats, waxes and other natural and synthetic fatty substances, preferably esters of fatty acids with alcohols of low C number, for example with isopropanol, propylene glycol or glycerol, or esters of fatty alcohols with alkanoic acids of low C number or with fatty acids; alkyl benzoates; silicone oils, such as dimethylpolysiloxanes, diethylpolysiloxanes, diphenylpolysiloxanes and mixed forms thereof.

If appropriate, the aqueous phase of the formulations according to the invention advantageously includes alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of poly-acrylates, preferably a polyacrylate from the group consisting of so-called Carbopols, for example Carbopols of types 980, 981, 1382, 2984 and 5984, in each case individually or in combination.

A preferred cosmetic formulation is a sunscreen composition. A sunscreen can advantageously additionally include at least one further UVA filter and/or at least one further UVB filter and/or at least one inorganic pigment, preferably an inorganic micropigment. The UVB filters can be oil-soluble or water-soluble. Advantageous oil-soluble UVB filter substances are, for example: 3-benzylidenecamphor derivatives, preferably 3-(4-methylbenzylidene)camphor and 3-benzylidenecamphor; 4-aminobenzoic acid derivatives, preferably 2-ethylhexyl 4-(dimethylamino) benzoate and amyl 4-(dimethylamino)benzoate; esters of cinnamic acid, preferably 2-ethylhexyl 4-methoxycinnamate and isopentyl 4-methoxycinnamate; derivatives of benzophenone, preferably 2-hydroxy-4-methoxybenzophenone, 2-hydroxy-4-methoxy-4'-methylbenzophenone and 2,2'-dihydroxy-4-methoxybenzophenone; esters of benzalmalonic acid, preferably di(2-ethylhexyl)4-methoxybenzalmalonate. Advantageous water-soluble UVB filter substances are, for example: salts of 2-phenylbenzimidazole-5-sulphonic acid, such as its sodium, potassium or its triethanolammonium salt, and the sulphonic acid itself; sulphonic acid derivatives of benzophenones, preferably 2-hydroxy-4-methoxybenzophenone-5-sulphonic acid and salts thereof; sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl)benzenesulphonic acid and salts thereof. The list of further UVB filters mentioned which can be used in combination with the active agent(s) according to the invention is not of course intended to be limiting.

Formulations for parenteral administration include a sterile aqueous preparation of the composition, or dispersions of sterile powders that include the composition, which are preferably isotonic with the blood of the recipient. Isotonic agents that can be included in the liquid preparation include sugars, buffers, and sodium chloride. Solutions of the composition can be prepared in water, and optionally mixed with a nontoxic surfactant. Dispersions of the composition can be prepared in water, ethanol, a polyol (such as glycerol, propylene glycol, liquid polyethylene glycols, and the like), vegetable oils, glycerol esters, and mixtures thereof. The ultimate dosage form is sterile, fluid and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the composition, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the composition by the animal over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active compound as a powder or granules, as liposomes containing the active compound, or as a solution or suspension in an aqueous liquor or non-aqueous liquid such as a syrup, an elixir, an emulsion or a draught.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active compound may be incorporated into sustained-release preparations and devices.

Methods of Use

The present invention is further directed to methods for treating certain conditions in ex vivo or in vivo cells. The conditions include, for instance, the presence of damaged bases in the cells, preferably skin cells, treating skin cancer, and treating UV induced immunosuppression, and are described in greater detail herein. The cell can be ex vivo or in vivo. As used herein, "ex vivo" refers to a cell that has been removed from the body of an animal. Ex vivo cells include, for instance, primary cells (e.g., cells that have recently been removed from a subject and are capable of limited growth in tissue culture medium), and cultured cells (e.g., cells that are capable of long term culture in tissue culture medium). Such ex vivo methods can be used in various applications, such as determining whether a polypeptide having identity to a polypeptide of the present invention has pyrimidine glycosylase activity, preferably, pyrimidine glycosylase/AP lyase activity. The cell is a eukaryotic cell, preferably, an animal cell, including human, as well as other animals (for instance, mice or rats,) that can be used as animal models in the study of the conditions described herein. Preferably, the cell is a human cell. Cell types that are useful in the methods disclosed herein include cells present in the epidermis, including, for instance, keratinocytes, squamous cells, basal cells, melanocytes, and Langerhans' cells.

Treatment of the conditions described herein can be prophylactic or, alternatively, can be initiated after the development of a condition described herein. Treatment that is prophylactic, for instance, initiated before a subject manifests symptoms of a condition described herein and/or before exposure to an agent that damages DNA, for instance, UV light, oxidative stress, alkylation damage and deamination, preferably UV light, is referred to herein as treatment of a subject that is "at risk" of developing the condition. Accordingly, administration of a composition can be performed before, during, or after the occurrence of the conditions described herein. Treatment initiated after the development of a condition may result in decreasing the severity of the symptoms of one of the conditions, or completely removing the symptoms. Non-limiting examples of subjects particularly suited to receiving the composition are those who may be exposed to natural or artificial UV irradiation, individuals having genetic deficiencies in polypeptides involved in DNA repair (for instance, those suffering from xeroderma pigmentosum), and individuals who are immunosuppressed due to disease states (such as AIDS) or transplantation.

A composition that is introduced to a cell, including introduced to a subject, that has or is at risk of developing a condition described herein includes an effective amount of a pyrimidine glycosylase including a targeting sequence. As used herein, an "effective amount" is an amount effective to decrease or prevent (for prophylactic treatment) in a subject the symptoms associated with a condition described herein. Preferably, the composition further includes a pharmaceutically acceptable carrier. Preferably, the composition is administered to the subject by topical administration.

An aspect of the invention is directed to a method for increasing the repair rate of damaged bases in a cell, preferably a skin cell. The method includes introducing to a skin cell exposed to or at risk of exposure to an agent that damages DNA a composition that includes an effective amount of a composition including a pyrimidine glycosylase, preferably a pyrimidine glycosylase/AP lyase, that includes a targeting sequence. The symptoms of this condition include, for instance, the increased presence of damaged DNA, increased mutagenesis rates, increased immunosuppression, increased tumor formation (for instance, increased actinic keratosis, increased basal cell carcinoma, and increased squamous cell carcinoma, and possibly increased melanoma), and increased incidence of apoptotic cells.

Whether the repair rate of damaged bases in a cell is increased can be determined by, for instance, assaying for the amount of damaged DNA in cells using a variety of techniques including coding sequence-specific repair assays (Bohr et al., Cell, 40, 359–369 (1985)), and photoproduct removal as determined by ELISA assays using antibodies directed against cis-syn dimers (Clarkson et al., Mutation Res., 112, 287–299 (1983)). Alternatively, when human cells are used, the removal of lesions can be assayed by quantitative PCR assay that is specific for human mitochondrial DNA (see Balleinger et al., Exp. Eye Res., 68, 765–772 (1999), and Ballinger et al., Circ, Res., 86, 960–966 (2000)). For instance, ex vivo cells can be exposed to an agent that damages DNA, preferably UV light, and treated with a composition including a polypeptide of the present invention. After a period of time sufficient to allow repair, the amount of damaged DNA in the cells can be determined and compared to the same type of cell that was not treated with the polypeptide. The presence of less damaged DNA in the cell treated with the polypeptide relative to the cell not treated indicates the polypeptide increases the repair rate of DNA. The repair rate of damaged DNA in in vivo cells may also be determined. For instance, an animal can be exposed to an agent that damages DNA, and treated with a composition including a polypeptide of the present invention. After a period of time sufficient to allow repair, skin biopsies are prepared and the amount of damaged DNA determined and compared to skin biopsies obtained from animals not treated with the polypeptide. The presence of less damaged DNA in cells in the biopsies treated with the polypeptide relative to cells in the biopsies not treated indicates the polypeptide increases the repair rate of DNA. Commonly accepted in vivo models are available for testing whether a polypeptide will increase the repair rate of DNA (for human models, see, for instance, Yarosh et al., Photochem. Photobiol., 69, 136–140 (1999); for animal models, see, for instance, Mitchell et al., J. Invest. Dermatol., 95, 55–59 (1990)).

The present invention further provides methods for treating mutagenesis in a cell, preferably a skin cell, in response to an agent that damages DNA, preferably UV light. In this aspect of the invention, mutagenesis rates are decreased. Mutagenesis results when repair of damaged DNA does not occur and, upon replication of the DNA, a different base is inserted. The method includes introducing to a skin cell exposed to or at risk of exposure to an agent that damages DNA a composition that includes an effective amount of a pyrimidine glycosylase, preferably a pyrimidine glycosylase/AP lyase, that includes a targeting sequence. Whether the rate of mutagenesis in a cell is reduced can be determined by, for instance, hprt mutagenesis assays (O'Neill et al, Mutat. Res., 45, 103–109 (1977)). Briefly, the measurement of mutagenesis using an hprt assay involves the selection of mammalian cells that are resistant to the killing effects of 6-thioguanine through a mutation in the hprt coding sequence. The assay relies on an inability of hprt-cells to activate 6-thioguanine for incorporation into DNA that results in cell killing. All cells with wild type hprt are killed upon 6-thioguanine selection. The cells can be in vivo or ex vivo. The rate of mutagenesis in cells treated with a polypeptide of the present invention can be determined and compared to the rate of mutagenesis in cells not treated. The presence of a lower mutagenesis rate in treated cells relative to untreated cells indicates the polypeptide decreases the mutagenesis rate of DNA.

Also provided by the present invention are methods for treating immunosuppression in a cell, preferably a skin cell, in response to an agent that damages DNA, preferably UV light. The presence of damaged DNA results in a temporary, reversible immunosuppression. The method includes introducing to a skin cell exposed to or at risk of exposure to an agent that damages DNA a composition that includes an effective amount of a pyrimidine glycosylase, preferably a pyrimidine glycosylase/AP lyase, that includes a targeting sequence. Whether immunosuppression in response to a DNA damaging agent is decreased can be determined by, for instance, measuring the transcription and/or translation of coding sequences that promote immunosuppression in response to a DNA damaging agent. For instance, the transcription and/or translation of a coding sequence encoding interleukin-10 (IL-10) or tumor necrosis factor alpha (TNFa) can be measured using Northern blot analyses or commercially available antibody kits. The immunosuppression in cells treated with a polypeptide of the present invention can be determined and compared to the immunosuppression in cells not treated. The presence of higher levels of IL-10 and/or TNFa in treated cells relative to untreated cells indicates the polypeptide decreases the immunosuppression of a cell in response to agents that damage DNA.

The present invention is also directed to methods for treating tumor formation in a cell, preferably a skin cell, in response to an agent that damages DNA, preferably UV light. In this aspect of the invention, tumor formation is decreased. The types of tumors that may occur in response to an agent that damages DNA include actinic keratosis, basal cell carcinoma, squamous cell carcinoma, and melanoma. The method includes introducing to a skin cell that is at risk of developing a tumor in response to an agent that damages DNA a composition that includes an effective amount of a pyrimidine glycosylase, preferably a pyrimidine glycosylase/AP lyase, that includes a targeting sequence. Cells at risk of developing a tumor in response to an agent that damages DNA include cells exposed to or at risk of exposure to an agent that damages DNA. Whether the formation of tumors in an animal is reduced can be determined by the use of animal models, for instance mice, that have been exposed to solar simulated light or exposure to sunlight. Solar simulated light is light having a spectral profile which is similar to natural solar irradiation, i.e. the emission spectrum of a solar simulator looks similar to spectrum of a solar noon day. Wavelengths of light include ~295–400 nm so is inclusive of UVA, UVB but not UVC which does not get through the ozone (see, for instance, Yoon et al., *J. Mol. Biol.*, 299, 681–693 (2000). The presence of a tumor can be determined by methods known in the art, and typically include cytological and morphological evaluation. The cells can be in vivo or ex vivo, including obtained from a biopsy. The rate of tumor formation in cells treated with a polypeptide of the present invention can be determined and compared to the rate of mutagenesis in cells not treated. The presence of a lower rates of tumor formation in treated cells relative to untreated cells indicates the polypeptide decreases tumor formation.

Another aspect of the present invention is directed to treating the formation of apoptotic cells, preferably apoptotic skin cells, in response to an agent that damages DNA, preferably UV light. Apoptotic cells are cells undergoing, or that have undergone, programmed cell death. In this aspect of the invention, the formation of apoptotic cells is decreased. The method includes introducing to a skin cell exposed to or at risk of exposure to an agent that damages DNA a composition that includes an effective amount of a pyrimidine glycosylase, preferably a pyrimidine glycosylase/AP lyase, that includes a targeting sequence. Whether the formation of apoptotic cells is reduced can be determined by, for instance, assays that detect apoptotic cells. Such assays include immunohistochemistry using antibodies against apoptotic-specific polypeptides associated with apoptotic cells, including, for instance, anti-caspase 8, anti-procaspase 9, and anti-G3PDH antibodies. Such antibodies are known to the art, and are available from, for instance, Trevigan (Gaithersberg, Md.) and Sigma (St. Louis, Mo.). The cells can be in vivo or ex vivo, including obtained from a biopsy. The formation of apoptotic cells in cells treated with a polypeptide of the present invention can be determined and compared to the formation of apoptitic cells in cells not treated. The presence of a lower apoptosis rate in treated cells relative to untreated cells indicates the polypeptide decreases the formation of apoptotic cells.

The present invention is illustrated by the following examples. It is to be understood that the particular examples, materials, amounts, and procedures are to be interpreted broadly in accordance with the scope and spirit of the invention as set forth herein.

EXAMPLES

Figure 2:
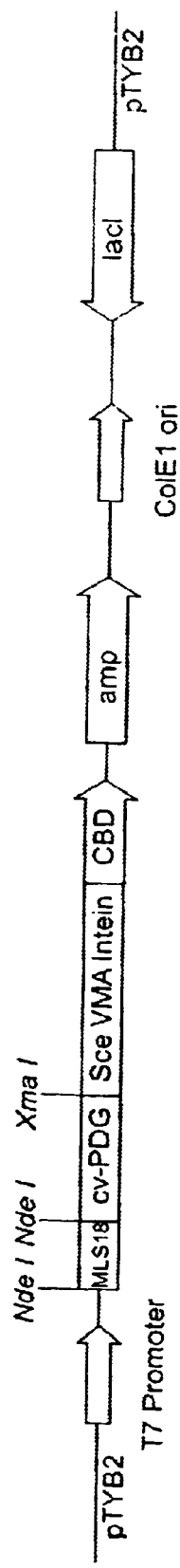
FIG. 2. Plasmid MLS18*-cv-pdg-pTYB2 (Out of frame fusion of MLS18, cv-pdg, intein, and chitin binding domain).

I. Mitochondrial Targeting of cv-pdg and T4-pdg
  A. Plasmid Constructs
    1. *E. coli* Expression
      a. Construction of a cv-pdg gene containing a mitochondrial localization signal (MLS18) sequence
        i. Plasmid construct The cv-pdg gene was cloned into expression vector pTYB2 as previously described (Garvish and Lloyd, *J. Mol. Biol.*, 295, 479–488 (2000)) to generate plasmid cv-pdg-pTYB2 (FIG. 1). Synthetic oligonucleotides were designed to encode 18 amino acids MALHSMRKARERWSFIRA (MLS18) (SEQ ID NO:1) that are identical to those found in the MLS of human mitochondrial tryptophanyl tRNA synthetase (HmtTrpRS) (Jørgensen et al., *J. Biol. Chem.*, 275, 16820–16826 (2000)). However, rather than using the specific DNA sequence found in this human gene, the oligonucleotides were designed using codons optimized for high-level expression in *E. coli*. These DNAs also contain sequences for cloning the MLS18 coding sequence into the NdeI site of the cv-pdg-pTYB2 plasmid. As designed, a correct insertion of this sequence yielded an out of frame fusion gene that was corrected in a subsequent step. For the construction of the MLS18, the following oligonucleotides were used: 5' T ATG GCG TTA CAT AGC ATG CGC AAA GCG CGC GAA CGC TGG AGC TTT ATT AGA GCA (SEQ ID NO:2) and 5' TA TGC TCT AAT AAA GCT CCA GCG TTC GCG CGC TTT GCG CAT GCT GTA TAA CGC CA (SEQ ID NO:3). Both oligonucleotides were purified by electrophoresis through a 15% polyacrylamide-8M urea gel in TBE buffer (89 mM Tris, 89 mM boric acid, 2 mM EDTA (pH 8.0)) for 4 h at 20 W. DNAs were visualized using UV shadow casting and purified as described by (Micro Bio Spin 6 column, BioRad). Each oligonucleotide was resuspended in water to a final concentration of 170–230 picomoles per microliter (pmol/$\mu$l) (1.1-1.5 $\mu$g/$\mu$l). Ten micrograms ($\mu$g) of each oligonucleotide were individually phosphorylated in a 30-$\mu$l reaction using 20 units of T4 DNA polynucleotide kinase (New England BioLabs, Beverly, Mass.) in 1×kinase buffer (70 mM Tris-HCl (pH 7.6), 10 mM $MgCl_2$, 5 mM DTT) supplemented with 100 micrograms per milliliter ($\mu$g/ml) BSA and 1 millimolar (mM) ATP, for 1 hour at 37° C. To generate double-stranded DNA, equal amounts (10 $\mu$g) of complementary oligonucleotides were annealed in a 60 $\mu$l volume by first heating at 90° C. for 1 minute in a heat block. The heat block was then removed from the heat source and placed on the bench-top to allow slow cooling overnight to room temperature. The double-stranded DNA was purified by phenol extraction followed by gel filtration chromatography (Micro Bio-Spin 6 column, BioRad). The annealed duplex oligonucleotides were inserted at the NdeI site in the plasmid cv-pdg-pTYB2, immediately upstream of the 5' end of the cv-pdg structural gene, to generate plasmid MLS18*-cv-pdg-pTYB2 (FIG. 2). A ligation reaction (with an insert: vector molar ratio of 10:1) was carried out at 16° C. for 12 hours in 1×ligase buffer (50 mM Tris-HCl (pH 7.8), 10 mM $MgCl_2$, 10 mM DTT, 1 mM ATP) using 400 units of T4 DNA ligase (New England BioLabs) per $\mu$g of DNA in a final volume of 20 $\mu$l. Small aliquots (1 $\mu$l –5 $\mu$l) of the ligation reaction were used to transform $CaCl_2$ competent DH5$\alpha$ *E. coli* (100 $\mu$l). Cells were made competent using standard protocols (Ausubel et al., (Eds.) *Current Protocols in Molecular Biology*, John Wiley & Sons, Inc. New York, N.Y. (1994)). The transformation reaction consisted of a 30 minute incubation of the cells with the DNA followed by 30 seconds at 42° C., and 2 minutes on ice. The cells were allowed to recover for 1 hour at 37° C. in 1 ml of SOC medium (2% Tryptone, 0.5% Yeast Extract, 10 mM NaCl, 2.5 mM KCl, 10 mM $MgCl_2$–$6H_2O$, 20 mM Glucose, pH 7.0). Small aliquots (50–100 $\mu$l) of the transformation reaction were plated on LB-plates containing ampicillin (100 $\mu$g/ml) and the plates were incubated overnight at 37° C.
      ii. Screening for recombinant plasmid clones Plasmid DNA was isolated for ten colonies from step 1a above using WIZARD PLUS MINIPREPS (Promega, Madison, Wis.) according to the manufacturer's protocol. The purified DNA was used as template for screening of plasmid clones with the MLS18 insert in the correct orientation using a polymerase chain reaction (PCR) with primers derived from a combination of the MLS sequence and from the cv-pdg gene. Only clones with the MLS18 insert in the correct orientation were expected to give a PCR product of the correct size (~550 bp). The following primer pair was used in the PCR for screening of recombinant clones: 5' ATA CGG GGTACC ACC ATG GCG TTA CAT AGC ATG CG 3' (KpnI-MLS18) (SEQ ID NO:4) and 5' GCA CGC GGA TCC TTA ATT ATT GCT GOT TTT AGC TTT CG 3' (BamHI-CV) (SEQ ID NO:5). Each 25 $\mu$l PCR reaction consisted of 10 ng of plasmid DNA, 10 pmol each primer, 12.5 mM each dNTP, 1 unit Taq DNA polymerase (Sigma, St. Louis, Mo.), and 1×PCR buffer components (Sigma: 10 mM Tris-HCl (pH 8.3), 50 mM KCl with 1.5 mM $MgCl_2$). The conditions of the PCR consisted of 2 minutes at 94° C. followed by 30 cycles of 94° C. for 30 seconds, 62° C. for 40 seconds, and 72° C. for 40 seconds. The PCR products were analyzed on a 1.5% TBE-agarose gel stained with ethidium bromide. Five plasmid clones with the MLS insert in the correct orientation were purified using Qiagen Plasmid Midi kit (Qiagen) according to the manufacturer's instructions and subjected to DNA sequencing (performed by the NIEHS Core facility, University of Texas—Medical Branch (UTMB), Galveston, Tex.).

iii. Site-directed mutagenesis

Figure 3:
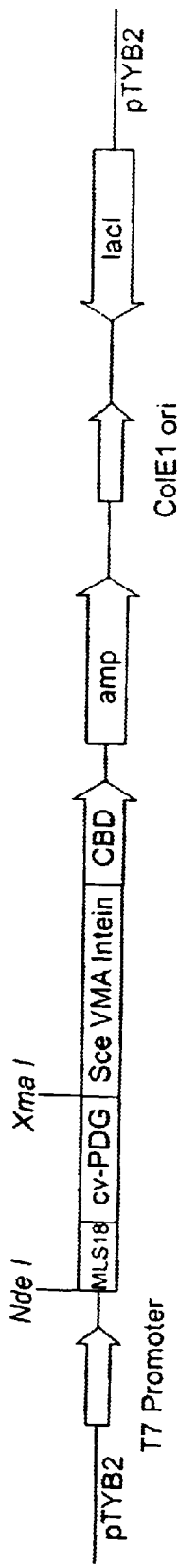
FIG. 3. Plasmid MLS18-cv-pdg-pTYB2 (In frame fusion of MLS18, cv-pdg, intein, and chitin binding domain).

Following DNA sequence verification, one plasmid clone with the MLS18 coding sequence was selected for use as template in PCR-mediated site-directed mutagenesis that allows the MLS18 to be in-frame with the structural gene encoding cv-pdg. The sequences of the primers used in the mutagenesis of the cv-pdg construct were as follows: 5' GC TTT ATT AGA GCA ACA CGT GTG AAT C (SEQ ID NO:6) and 5' GAT TCA CAC GTG TTG CTC TAA TAA AGC (SEQ ID NO:7). Each 50 µl PCR reaction contained 25–50 nanograms (ng) template DNA, 20 pmol each primer, 25 mM each dNTP, 2.5 units Cloned Pfu Turbo DNA polymerase (Stratagene, La Jolla, Calif.) in 1×Pfu Turbo PCR buffer (10 mM KCl, 10 mM $(NH_4)_2SO_4$ 20 mM Tris-HCl (pH 8.75) 2 mM Mg $SO_4$, 0.1% Triton X-100, 0.1 mg/ml BSA) (Stratagene). The conditions of the PCR consisted of 4 minutes at 94° C. prior to the addition of Cloned Pfu Turbo DNA polymerase (Stratagene) followed by 20 cycles of 95° C. for 40 seconds, 52–58° C. for 1 minutes, and 68° C. for 15 minutes. Successful PCR was verified using agarose gel electrophoresis followed by staining with ethidium bromide. DNA from successful PCR was purified using QIAquick PCR Purification Kit (Qiagen, Valencia, Calif.), eluted in double distilled $H_2O$ (dd$H_2O$), and treated with 20 units DpnI (New England BioLabs) per microgram of DNA at 37° C. for 2 hours. Small aliquots (1–5 µl) of the DpnI-treated reaction were used to transform XL-1 Blue Supercompetent cells (Stratagene) according to the manufacturer's instructions. Various aliquots (100 µl–200 µl) of the transformation reaction were plated on LB plates containing ampicillin (100 µg/ml). Plasmid DNA was prepared for four ampicillin-resistant colonies using Qiagen Plasmid Midi Kit (Qiagen) and the mutagenesis was verified using automated DNA sequencing (NIEHS Core facility). One plasmid clone with the MLS18 correctly fused in frame to cv-pdg gene (FIG. 3) was used to transform E. coli ER2566 (New England BioLabs) for expression of the MLS18-cv-pdg fusion protein.

b. Construction of a T4-pdg gene containing a mitochondrial localization signal (MLS18) sequence.

i. Plasmid construct

Figure 4:
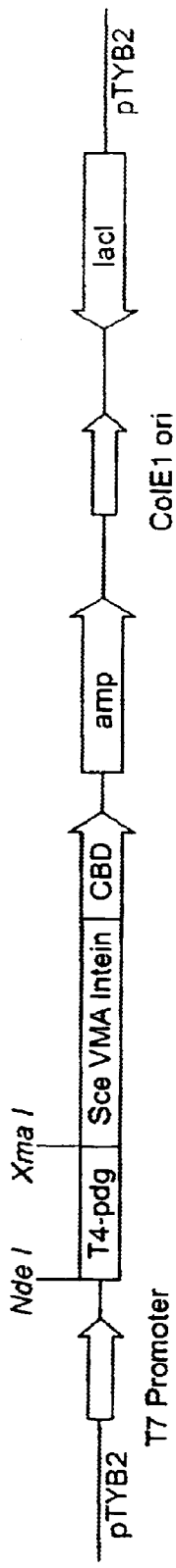
FIG. 4. Plasmid T4-pdg-pTYB2 (In frame fusion of T4-pdg, intein and chitin binding domain).
Figure 5:
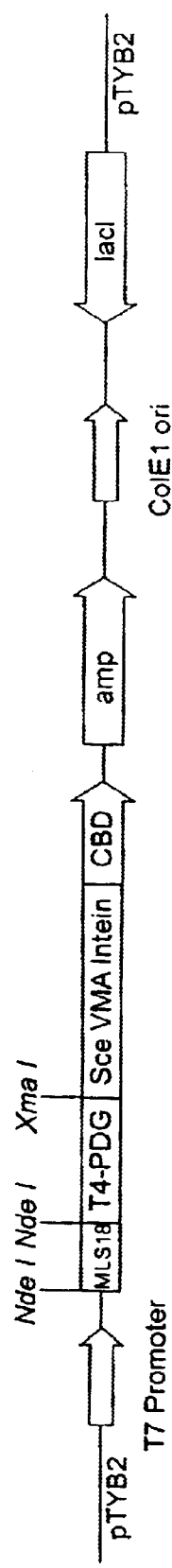
FIG. 5. Plasmid MLS18-T4-pdg-pTYB2 (Out of frame fusion of MLS18, T4-pdg, intein, and chitin binding domain).

The T4-pdg gene was cloned into expression vector pTYB2 as previously described (Garvish and Lloyd, J. Mol. Biol., 295, 479–488 (2000)) to generate plasmid T4-pdg-pTYB2 (FIG. 4). Cloning of the MLS18 to the NdeI site of T4-pdg-pTYB2 was performed as described above to generate plasmid MLS18*-T4-pdg-pTYB2 (FIG. 5).

ii. Screening for recombinant plasmid clones

Plasmid DNA was isolated for ten colonies using Promega WIZARD PLUS MINIPREP (Promega) according to the manufacturer's protocol. Screening of recombinant clones with the MLS18 insert in the correct orientation was performed as described above, except that one primer was derived from the T4-pdg sequence. The following primer pair was used in the PCR for screening of recombinant clones: 5' ATA COG GGTACC ACC ATG GCG TTA CAT AGC ATG CG (KpnI-MLS18) (SEQ ID NO:8) and 5' GCA CGC GGA TCC TTA TGC ATA AAT CGC CTT ACC G 3' (BamHI-T4) (SEQ ID NO:9). Three plasmid clones with the MLS insert in the correct orientation were purified using Qiagen Plasmid Midi kit (Qiagen) according to the manufacturer's instructions and subjected to DNA sequencing (performed by the NIEHS Core facility).

iii. Site-directed mutagenesis

Figure 6:
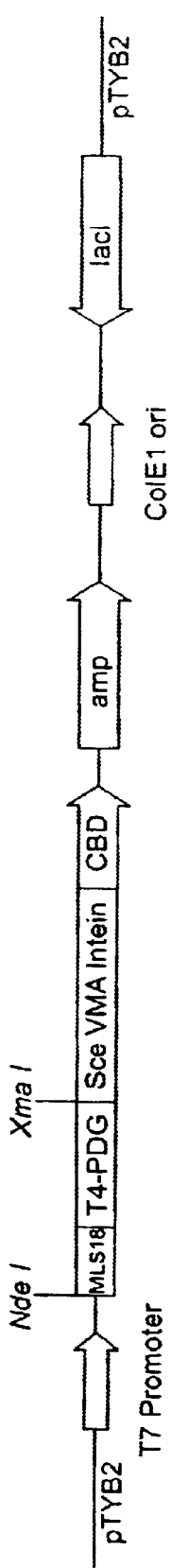
FIG. 6. Plasmid MLS18-T4-pdg-pTYB2 (In frame fusion of MLS18, T4-pdg, intein, chitin binding domain).

One plasmid clone with the MLS18 of the correct sequence and orientation was selected for use as template in a PCR-mediated site-directed mutagenesis that allows the MLS to be in-frame with the structural gene encoding T4-pdg. Site directed mutagenesis was performed essentially as described above, except a primer pair with the following sequences was used: 5' GC TTT ATT AGA GCA ACT CGT ATC AAC C (SEQ ID NO:10) and 5' GGTT GAT ACG AGT TGC TCT AAT AAA GC (SEQ ID NO:11). Plasmid DNA was prepared from four recombinant clones using Qiagen Plasmid Midi Kit (Qiagen) and the mutagenesis was verified using automated DNA sequencing (NIEHS Core facility). One plasmid clone with the MLS18 correctly fused in frame to the T4-pdg gene (FIG. 6) was used to transform E. coli ER2566 (New England BioLabs) for expression of the MLS18-T4-pdg fusion protein.

c. Construction of a cv-pdg gene containing a mitochondrial localization signal (MLS35) sequence.

i. Plasmid construct

Figure 7:
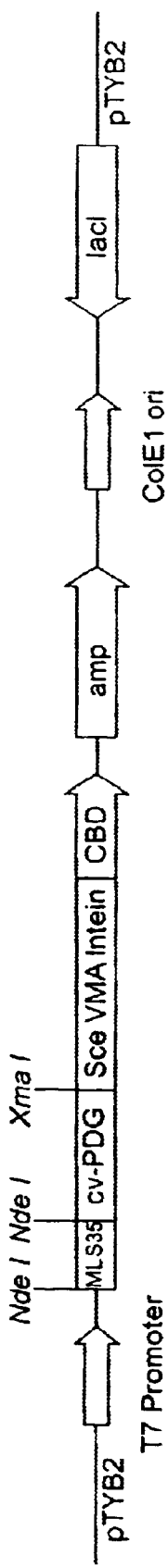
FIG. 7. Plasmid MLS35*-cv-pdg-pTYB2 (Out of frame fusion of MLS35, cv-pdg, intein and chitin binding domain).

Synthetic oligonucleotides with sequences for the MLS of human uracil-DNA glycosylase (UNG1) (containing a 35 amino-acid signal) (Otterlei et al., Nucl. Acids Res., 26, 4611–4617 (1998)) were designed to contain codons for high-level expression in E. coli and sequences for cloning into the NdeI site of the plasmid cv-pdg-pTYB2. The following oligonucleotides were used for the construction of MLS35: 5' TAT GGG CGT GTT TTG CTT AGG CCC GTG GGG CTT AGG CCG CAA ATT ACG CAC CCC GGG CAA AGG CCC GTT ACA GTT ATT ATC GCG CTT ATG CGG CGA TCA TTT ACA G (SEQ ID NO:12) and 5' TAC TGT AAA TGA TCG CCG CAT AAG CGC GAT AAT AAC TGT AAC GGG CCT TTG CCC GGG GTG COT AAT TTG COG CCT AAG CCC CAC GGG CCT AAG CAA AAC ACG CCC A (SEQ ID NO:13). Both oligonucleotides were purified as described above and resuspended in water to give final concentrations of 0.25 nmol/µl. Each oligonucleotide was individually phosphorylated then combined for annealing as described above. The annealed DNA was loaded onto a 2% TBE-agarose gel run for 1.5 hours at 4V/cm along with a DNA standard (100 bp Ladder, New England Biolabs), and stained with ethidium bromide. The stained DNA of the correct size was excised, extracted using Qiagen Gel Extraction kit (Qiagen), and resuspended in dd$H_2O$. Double-stranded MLS35 DNA was then inserted into the NdeI site of cv-pdg-pTYB2 (FIG. 7) as described above, except the ligation reaction was carried out at 4° C. overnight. The amino acid sequence of the encoded MLS35 was MGVF-CLGFWGLGRKLRTFGKGPKQLLSRLCGDHLQ (SEQ ID NO:47).

ii. Screening of recombinant plasmid clones

Plasmid DNA was isolated for ten colonies using Promega WIZARD PLUS MINIPREP (Promega) according to the manufacturer's protocol. The purified DNA was used as template for screening of plasmid clones with the MLS35 insert in the correct orientation using PCR with primers derived from the MLS sequence and from the cv-pdg gene.

Screening for recombinant clones with the MLS35 insert in the correct orientation was performed as described above using specific primers derived from the MLS35 sequence and from the cv-pdg sequence. A PCR product of ~600 bp was expected for clones with the MLS insert in the correct orientation. The following primer pair was used: 5' ATA CGG GGT ACC ACC ATG GGC GTG TTT TGC TTA GG (KpnI-MLS35) (SEQ ID NO:14) and 5' GCA CGC GGA TCC TTA ATT ATT GCT GGT TTT AGC TTT CG (BamHI-CV) (SEQ ID NO:15). Five clones with the MLS35 in the correct orientation were selected for plasmid isolation (Qiagen Plasmid Midi Kit, Qiagen) and the purified DNA subjected to automated DNA sequencing (performed by the NIEHS Core facility).

iii. Site-directed mutagenesis

Figure 8:
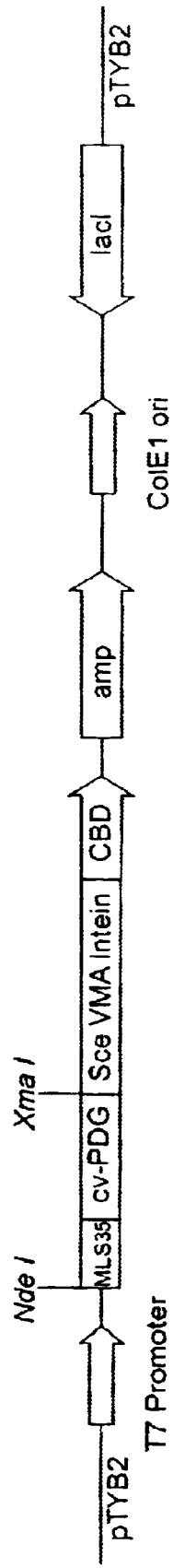
FIG. 8. Plasmid MLS35*-cv-pdg-pTYB2 (In frame fusion of MLS35, cv-pdg, intein and chitin binding domain).

One plasmid clone with the MLS35 of the correct sequence (FIG. 7) was selected for use as template in PCR-mediated site-directed mutagenesis. Site directed mutagenesis was performed essentially as described above, except a primer pair with the following sequences was used: 5' GGC GAT CAT TTA CAG ACT CGA GTG AAT CTC GTA CCG (cv-pdg forward) (SEQ ID NO:16) and 5' CGG TAC GAG ATT CAC TCG AGT CTG TAA ATG ATC GCC (cv-pdg reverse) (SEQ ID NO:17). Plasmid DNA was prepared for four recombinant clones using Qiagen Plasmid Midi Kit (Qiagen) and the mutagenesis was verified using automated DNA sequencing (NIEHS Core facility). One plasmid clone with the MLS35 correctly fused to the cv-pdg gene (FIG. 8) was used to transform *E. coli* ER2566 (New England BioLabs) for expression of the MLS35-cv-pdg fusion protein.

d. Construction of a T4-pdg gene containing a mitochondrial localization signal (MLS35) sequence.

i. Plasmid construct

Figure 9:
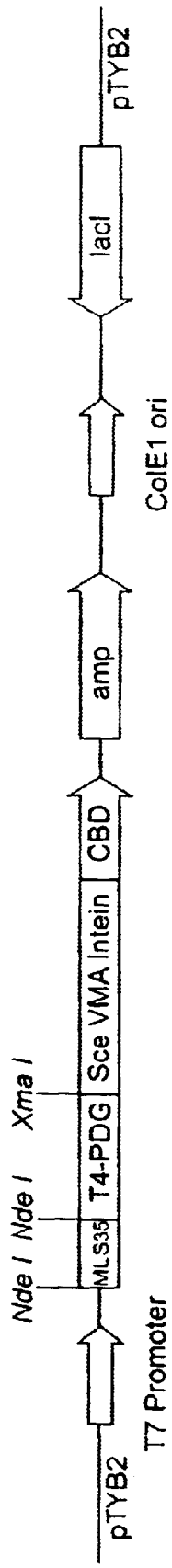
FIG. 9. Plasmid MLS35*-T4-pdg-pTYB2 (Out of frame fusion of MLS35, T4-pdg, intein and chitin binding domain).

Cloning of the DNA encoding MLS35 to T4-pdg-pTYB2 was performed as described above to generate plasmid MLS35-T4-pdg-pTYB2 (FIG. 9).

ii. Screening of recombinant plasmid clones

Ten colonies were selected for plasmid isolation using Promega WIZARD PLUS MINIPREP (Promega) according to the manufacturer's protocol. Screening of recombinant clones with the MLS35 insert in the correct orientation was performed essentially as described above using specific primers derived from the MLS35 sequence and from the T4-pdg sequence. A PCR product of ~600 bp was expected for clones with the MLS insert in the correct orientation. The following primer pair was used: 5' ATA CGG GGT ACC ACC ATG GGC GTG TTT TGC TTA GG (KpnI-MLS35) (SEQ ID NO:18) and 5' GCA CGC GGA TCC TTA TGC ATA AAT CGC CTT ACC G (BamHI-T4) (SEQ ID NO:19). Four clones with the MLS35 in the correct orientation were selected for plasmid isolation (Qiagen Plasmid Midi Kit) and the purified DNA subjected to automated DNA sequencing (performed by the NIEHS Core facility, UTMB).

iii. Site-directed mutagenesis

Figure 10:
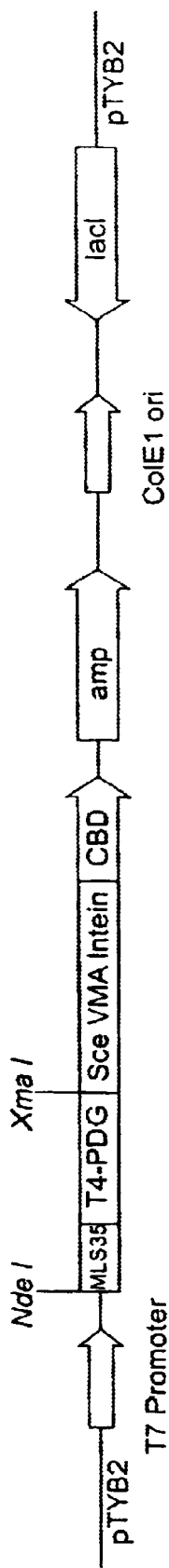
FIG. 10. Plasmid MLS35-T4-pdg-pTYB2 (In frame fusion of MLS35, T4-pdg, intein and chitin binding domain).

One plasmid clone with the MLS35 of the correct sequence (FIG. 9) was selected for use as template in PCR-mediated site-directed mutagenesis. Site directed mutagenesis was performed essentially as described above, except a primer pair with the following sequences was used: 5' GGC GAT CAT TTA CAG ACT COT ATC AAC CTT AC (T4 forward) (SEQ ID NO:20) and 5' GTA AGG TTG ATA CGA GTC TGT AAA TGA TCG CC (T4 reverse) (SEQ ID NO:21). Plasmid DNA was prepared from four recombinant clones using Qiagen Plasmid Midi Kit (Qiagen) and the mutagenesis was verified using automated DNA sequencing (NIEHS Core facility). One plasmid clone with the MLS35 correctly fused in frame to the T4-pdg gene (FIG. 10) was used to transform *E. coli* ER2566 (New England BioLabs) for expression of the MLS-T4-pdg fusion protein.

2. Mammalian Expression a. Construction of MLS18-cv-pdg-pEGFP-N3

Figure 11:
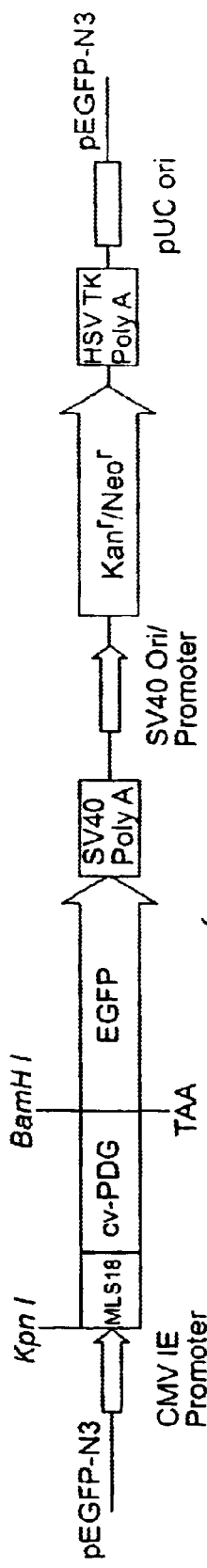
FIG. 11. Plasmid MLS18-cv-pdg*-x-pEGFP-N3 (In frame fusion of MLS18 and cv-pdg, with a stop codon between cv-pdg and EGFP).
Figure 12:
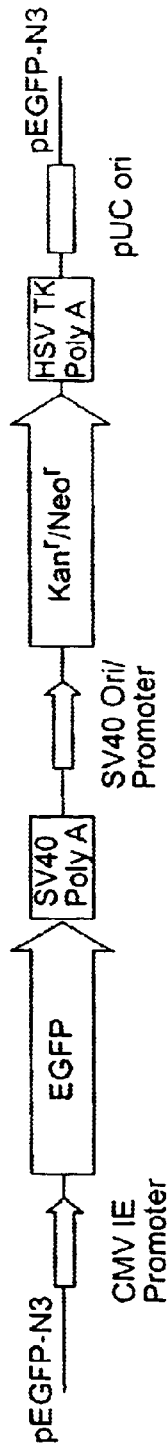
FIG. 12. Plasmid pEGFP-N3 (commercial vector from ClonTech).

In order to express various forms of these DNA glycosylases in mammalian cells, the ClonTech pEGFP-N3 vector that uses the cytomegalovirus immediate early (CMVIE) promoter was used. However, all the constructs using this vector were not be made as a fusion gene with the enhanced green fluorescent protein (EGFP). However, those constructs have been made in the laboratory that have the various repair genes fused with EGFP. Plasmid MLS18-cv-pdg-pEGFP-N3 (FIG. 11) was constructed by inserting a DNA sequence encoding the MLS18-cv-pdg into the KpnI and BamHI sites of vector pEGFP-N3 (ClonTech) (FIG. 12). The DNA sequence encoding MLS18-cv-pdg was PCR amplified using plasmid MLS18-cv-pdg-pTYB2 (FIG. 13) as template. The primers used in amplifying the MLS18-cv-pdg DNA fragment were designed to contain sequences for cloning into vector pEGFP-N3 and for optimal translation efficiency in mammalian cells. The sequences for the primers were as follows: 5' ATA COG GGTACC ACC ATG GCG TTA CAT AGC ATG CG (MLS18-Forward) (SEQ ID NO:22) and 5' GCA CGC GGATCC TTA ATT ATT GCT GGT TTT AGC TTT CG (CV-Reverse) (SEQ ID NO:23). Each 25 µl-PCR tube consisted of 10 ng template DNA, 10 pmol each primer, 1.25 mM each dNTP, 1.25 units Cloned Pfu Turbo DNA polymerase (Stratagene) in 1×Cloned Pfu Turbo PCR buffer (Stratagene). The reaction mixture was subjected to 2 minutes at 95° C. prior to the addition of the DNA polymerase followed by 30 cycles of 95° C. for 30 seconds, 62° C. for 40 seconds, and 68° C. for 2 minutes. For ligation into vector pEGFP-N3, the PCR product was first purified using QIA quick PCR Purification kit (Qiagen) and eluted in ddH$_2$O to a concentration of 25 ng/µl. The purified DNA (750 ng) was then digested sequentially with 8 units of BamHI for 4 hours and 10 units KpnI for 4 hours at 37° C. in a 35 µl-reaction containing appropriate buffers supplemented with BSA (0.1 mg/ml) as suggested by the enzyme supplier (New England BioLabs). The digested DNA was purified using silica matrix (GeneClean II, Quantum Biotechnologies, Carlsbad, Calif.) and resuspended in ddH$_2$O to a concentration of 20 ng/µl. To prepare vector pEGFP-N3 for ligation, 2 µg of vector DNA was sequentially digested with 8 units of BamHI for 4 hours and with 10 units of KpnI for 4 hours at 37° C. in a 25 µl-reaction. Digested vector DNA was then purified by phenol extraction, resuspended in ddH$_2$O, and subjected to treatment with 0.1 unit of calf intestinal alkaline phosphatase (CIAP) for 1 hour at 37° C. in a 25 µl-reaction in 1×reaction buffer (20 mM Tris-acetate, 10 mM magnesium acetate, 50 mM potassium acetate, 1 mM DTT). The reaction was stopped by adding EDTA to a final concentration of 50 mM and heating at 75° C. for 20 minutes. The CIAP-treated vector DNA was then extracted with phenol, purified using Gene Clean II kit (Quantum Biotechnologies) as instructed by the manufacturer, and resuspended in ddH$_2$O to a concentration of 50 ng/µl. The MLS18-cv-pdg insert was ligated to prepared vector at a 3:1 (insert:vector) molar ratio at 14° C. overnight in a 10 µl-reaction consisting of 200 ng vector DNA, 60 ng insert DNA, 400 units T4 DNA ligase (New England Biolabs) in 1×T4 Ligase buffer (New England Biolabs). A small aliquot (2 µl) of the ligation reaction was used to transform *E. coli* DH5α (100 µl) as previously described and small aliquots (100–200 µl) of the transformation reaction were plated on LB plates containing kanamycin (30 µg/ml). Plasmid DNAs from four kanamycin-resistant colonies were isolated using Qiagen Plasmid Midi Kit (Qiagen) and analyzed by automated DNA sequencing. One plasmid clone with the correct sequence (FIG. 11) was used to transfect a human cell line, HeLa-S3. As a control, the wild type cv-pdg gene without the MLS18 sequence was cloned into vector pEGFP-N3 using the same conditions, except plasmid cv-pdg-pTYB2 and a primer derived from the 5' end of cv-pdg gene were used in the PCR, to generate plasmid cv-pdg-pEGFP-N3 (FIG. 13). For amplification of the wild type cv-pdg gene, a forward primer with a sequence of 5' ATA CGG GGTACC ACC ATG ACA CGT GTG AAT CTC G (wt-CV-Forward) (SEQ ID NO:24) was used along with the CV-Reverse primer.

b. Construction of MLS18-T4-pdg-pEGFP-N3

Plasmid MLS18-T4-pdg-pEGFP-N3 (FIG. 14) was constructed using the same procedures and conditions as in the construction of MLS18-cv-pdg-pEGFP-N3, except for the use of plasmid MLS18-T4-pdg-pTYB2 (FIG. 6) as template and a reverse primer in the PCR to amplify the MLS18-T4-pdg DNA insert. The sequence for the primer used in the PCR amplification of MLS18-T4-pdg fragment is as follows: 5' GCA CGC GGATCC TAA TGC ATA AAT CGC CTT ACC G (T4-reverse) (SEQ ID NO:25). The wild type T4-pdg gene without the MLS18 sequence was also cloned into vector pEGFP-N3 (FIG. 15) using the same conditions, except plasmid T4-pdg-pTYB2 and a primer derived from the 5' end of T4-pdg gene was used in the PCR, to generate plasmid T4-pdg-pEGFP-N3 (FIG. 13). For amplification of the wild type T4-pdg gene, a forward primer with a sequence of 5' GA CGG GGTACC ACC ATG ACT CGT ATC AAC CTT ACT TTA GTA TCT G (wt-T4-Forward) (SEQ ID NO:26) was used along with the T4-Reverse primer.

B. Protein Expression and Purification

1. *E. coli*

The expression and purification of the recombinant proteins from transformed ER2566 *E. coli* was performed as suggested by the manufacturer (New England BioLabs). Briefly, cultures of 0.7 O.D.$_{600}$ were induced with isopropyl-1-thio-β-D-galactoside (IPTG) (final concentration 0.3 mM) for seven hours at 20–25° C. The cells were harvested by centrifugation at 5000×g for 10 min and the cell pellet resuspended in buffer A (20 mM HEPES, pH 8.0, 0.5 M NaCl, 0.1 mM EDTA, 0. 1% Triton X-100). The cells were disrupted using a French Press with constant pressure of 9000 p.s.i. and the cell lysate cleared of cellular debris by centrifugation at 12,000×g for 30 min. The cleared lysate was applied to a chitin bead column (New England BioLabs) that had been pre-equilibrated with buffer B (20 mM HEPES, pH 8.0, 0.5 M NaCl, 0.1 mM EDTA). The column was washed with buffer B and flushed with buffer C (20 mM HEPES, pH 8.0, 50 mM NaCl, 0.1 mM EDTA) containing 30 mM DTT. Following overnight incubation at room temperature, the recombinant protein was eluted with buffer B and the collected fractions were monitored for the target protein by polyacrylamide-SDS gels and staining with Coomassie Brilliant Blue R-250. The fractions that contained the recombinant protein were pooled, dialysed in buffer E (25 mM sodium phosphate, pH 8.0, 50 mM NaCl, 0.1 mM EDTA), and concentrated using an Amicon YM10 membrane (Millipore, Bedford, Mass.). The purity and the size of the recombinant proteins were assessed using 15% polyacrylamide-SDS gels along with purified wild type-T4-pdg and wild type-cv-pdg as controls. The gel was run at 15 mA for 5 hours in 1×Tris-Glycine buffer and subsequently stained with Coomassie Blue R-250. The addition of the ML18 corresponded to the mobility shift seen in MLS18-PDGs when compared to the wild-type PDGs. All purified recombinant proteins were stored in dialysis buffer E at 4° C.

Purified MLS18-T4 pdg and MLS18-cv-pdg enzymes were separated by electrophoresis on a 12% polyacrylamide-SDS gel and the proteins were transferred to PVDF membrane (Pharmacia) using 1×transfer buffer (100 mM Glycine, 10 mM Tris, 10% methanol). The proteins bound to the membrane were stained with Coomassie Brilliant Blue R-250 and subjected to N-terminal sequencing (performed by the Protein Chemistry Laboratory, UTMB) to verify that the correct MLS amino acid sequence had been properly expressed in *E. coli*. All sequences were determined to be exactly as expected.

C. Enzymatic Activity

1. Enzymatic activity assays of the purified enzymes containing the MLS.

As described previously, the addition of a MLS sequence onto the N-terminus will produce catalytically inactive enzymes that will be restored to full catalytic activity after the protein is imported into the mitochondria and the MLS sequence is removed. The proteolytic cleavage of the MLS sequence will yield a wild type enzyme inside the mitochondria where it can initiate repair of UV-induced DNA lesions. In order to verify that the added MLS sequences on the N-terminus of cv-pdg and T4-pdg inactivated the enzymatic activity, the ability of these pure proteins to incise plasmid DNA containing UV-induced pyrimidine dimers was tested. Standard in vitro plasmid nicking assays were performed using a protocol previously described (Garvish and Lloyd, *J. Mol. Biol.*, 295, 479–488 (2000)) with the following modifications. To prepare the substrate for the nicking assays, plasmid DNA pBR322 was diluted in TE buffer to give a concentration of 0.3 µg/µl and was UV-irradiated for 5 min at 100 µW/cm$^2$ to induce the formation of ~10 cyclobutane pyrimidine dimers (CPDs) per molecule. All recombinant enzymes were diluted to various concentrations in 1×reaction buffer consisting of 25 mM NaH$_2$PO$_4$ (pH 6.8), 125 mM NaCl, 1 mM EDTA, and 0.1 mg/mL bovine serum albumin (BSA). As a positive control in the nicking assays, wild-type T4-pdg was diluted to the same concentrations as the recombinant enzymes. Each 20 µl-nicking reaction consisted of 0.6 µg UV-irradiated DNA and a pre-determined concentration of the engineered enzymes (or wt-T4-pdg) in 1×reaction buffer. After a 30 minute incubation at 37° C., the reactions were stopped by adding an equal volume of loading buffer (25% Ficoll, 2% SDS). Half of the reaction was loaded on a 0.8% TBE-agarose gel and the products of the nicking reaction were visualized after staining with ethidium bromide. These data proved that the catalytic activity of the MLS engineered proteins was decreased approximately 4 orders of magnitude (an ~10,000-fold reduction), thus, rendering the enzymes essentially inactive.

D. Mammalian Cell Expression

1. Stable Transfectants a. Transfection of HeLa-S3 with DNA Constructs for Biological Assays HeLa-S3 cells were obtained from American Type Culture Collection (ATCC) and were maintained in high-glucose Dulbecco's Modified Eagle Media (DMEM) (Gibco, Rockville, Md.) supplemented with 10% fetal bovine serum (Gibco), 2 mM L-glutamine (Gibco), and 1×Gibco's antibiotic/antimycotic solution (100 units/ml penicillin G sodium, 100 µg/ml streptomycin sulfate, 0.25 µg/ml amphotericin B). The cells were grown in a humidified atmosphere with 5% $CO_2$ at 37° C. and were passaged every 3–4 days. For transfection, cells were grown in 35 mm dishes until they reached 50% confluence. The cells were then transfected with plasmids MLS18-cv-pdg-pEGFP-N3 and MLS18-T4-pdg-pEGFPN-3 using LipofectAMINE Plus Reagent (Gibco) according to the manufacturer's recommendations. Stable cell lines were established by the addition of selective reagent G148 (Geniticin, Mediatech, Herndon, Va.) to the growth medium (0.4 mg/ml) at 48 hours post-transfection. After 10 days, the transfected cells were maintained in 0.2 mg/ml G148. As controls, plasmids cv-pdg-pEGFP-N3 and T4-pdg-pEGFP-N3, and vector pEGFP-N3 were also used to transfect HeLa-S3 cells and stable cells lines established as described above.

2. Protein Chaperone

In order to initiate the repair of UV-induced DNA lesions in human cells by the base excision repair pathway, and specifically to initiate repair on mitochondrial DNA, it is necessary to deliver it into the cell of interest. To serve as a proof of principle, cultured HeLa-S3 cells were transfected with the purified enzymes using CHARIOT Transfection reagent as instructed by the manufacturer (Active Motif, Carlsbad, Calif.). CHARIOT is a transfection reagent capable of delivering proteins into cultured human cell lines. Briefly, HeLa-S3 cells were grown on 25 mm cover slips placed in 35 mm culture dishes at 37° C. in a humidified atmosphere containing 5% $CO_2$ until the cells are 50% confluent. Various amounts (0.25 µg–2 µg) of the control, unmodified wild-type enzymes and the purified MLS18 containing enzymes were complexed to the CHARIOT Reagent and the Chariot-enzyme complexes were overlayed onto the cells. Following 1.5 hour–3 hour incubation at 37° C. in a humidified atmosphere containing 5% $CO_2$, the cells were fixed for 10 minutes with acetone:methanol (1:1) and subjected to immunostaining.

3. Preparation of Mitochondrial Lysates for DNA Nicking Assays

Mitochondria from non-transfected cells (control) and transfected cells expressing MLS18-cv-PDG and MLS18-T4-PDG were purified as previously described (Yang et al., Science 275, 1129–1132 (1997)). Briefly, ~1.1×10⁷ cells were trypsinized, collected by centrifugation at 750×g for 5 minutes, and washed once with ice cold PBS. The cell pellet was then resuspended in sucrose-buffer A (20 mM HEPES, pH 7.5, 10 mM KCl, 1.5 mM MgCl2, 1 mM EDTA, 1 mM EGTA, 1 mM DTT, 0.1 mM PMSF) and 250 mM sucrose. The cells were lysed with a homogenizer so that at least 70% of cells were broken. The homegenate was centrifuged twice at 750×g at 4° C. for 10 minutes to remove unbroken cells, nuclei, and cell debris. The supernatant from this step was centrifuged at 7,800×g at 4° C. for 30 minutes and the mitochondrial pellet washed twice with sucrose-buffer A. For preparation of mitochondria lysate for DNA nicking assays, the mitochondrial pellet was lysed in for 5 minutes at room temperature 0.2 ml buffer A (without sucrose) containing 0.5% CHAPS. The sample was then centrifuged at 15,000×g for 30 minutes at 4° C. to obtain a clear lysate. Small amounts of this clear lysate and its dilutions were tested for DNA nicking activity. No pyrimidine dimer specific activity was detected in the control HeLa S3 cells, while two independent clones, one expressing MLS18-T4-pdg and one expressing MLS18-cv-pdg, both showed dimer-specific nicking. These data prove that the MLS sequences target these enzymes to the mitochondria and that they were processed to yield active enzymes.

II. Nuclear Targeting of cv-pdg and T4 pdg

A. Plasmid Constructs

1. *E. coli* Expression Constructs for NLS8a-cv-pdg Constructs a) Construction of a cv-pdg Gene Containing a Nuclear Localization Sequence (NLS)

The cv-pdg gene was cloned into expression vector pTYB2 as previously described (Garvish and Lloyd, *J. Mol. Biol.*, 295, 479–488 (2000)) to generate plasmid cv-pdg-pTYB2 (FIG. 1). Synthetic oligonucleotides were designed to encode a consensus NLS made up of 8 amino acids, PKKRKRRL (NLS8a) (SEQ ID NO:27). These DNAs also contained sequences for cloning the NLS-8a coding sequence into the XmaI site of the cv-pdg-pTYB2 plasmid. As designed, this sequence contains a stop codon (TAG) that prevents production of cv-pdg protein as a fusion with the chitin binding domain if the NLS8a sequence was ligated in the reverse orientation. For the construction of the NLS8a, the following oligonucleotides were used: 5'

5'CCGGGCCAAAGAAGAGGAAAAGGAGGCTA (SEQ ID NO:28), and c

5'CCGGG                          (SEQ ID NO:29).
TAGCCTCCTTTTCCTCTTCTTTGGC

Each oligonucleotide was resuspended in water to a final concentration of 212 pmol/µl and 202 pmol/µl, respectively. To generate double-stranded DNA, equal amounts (~200 pmoles) of complementary oligonucleotides were annealed in 20 µl containing DNA, T4 ligase buffer (1×composition: 50 mM Tris-HCl pH 7.5, 10 mM $MgCl_2$, 10 mM dithiothreitol, 1 mM ATP 25 µg/µl bovine serum albumin (BSA)) and 16 µl $ddH_2O$ by first heating at 90° C. for 3 minutes in a heat block. The heat block was then removed from the heat source and placed on the bench-top to allow slow cooling overnight at room temperature. The final concentration of NLS8a in this reaction was 10 pmol/µl.

Figure 16:
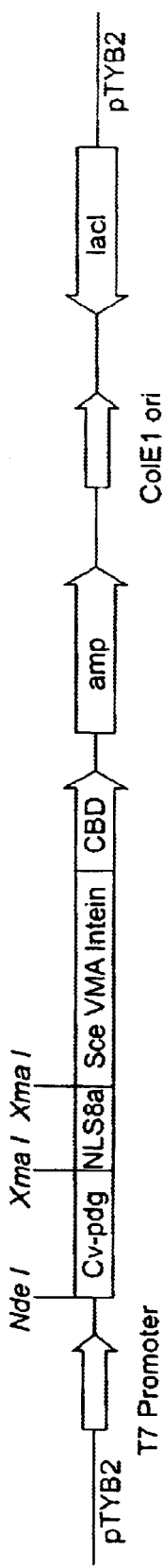
FIG. 16. Plasmid cv-pdg-NLS8a-pTYB2 (In-frame fusion of cv-pdg, NLS8a, intein and chitin binding domain).

The annealed duplex oligonucleotides were inserted at the XmaI site in the plasmid cv-pdg-pTYB2, immediately following the coding sequence for the cv-pdg structural gene, to generate plasmid cv-pdgNLS8a-pTYB2 (FIG. 16).

A ligation reaction was carried out at 16° C. for 72 hours in 1×ligase buffer (50 mM Tris-HCl (pH 7.8), 10 mM $MgCl_2$, 10 mM DTT, 1 mM ATP), 1 µl (2,000 Units) T4 Ligase (New England Biolabs, Beverly, Mass.), 1 µl of 100 mM ATP, and 5 µl $ddH_2O$.

A total of 5 µl of each ligation reaction were used to transform $CaCl_2$ competent DH5α*E. coli* (200 µl). Cells were made competent using standard protocols (Ausubel et al., (Eds.) *Current Protocols in Molecular Biology*, John Wiley & Sons, Inc. New York, N.Y. (1994)). The transformation conditions consisted of a 40 minutes incubation of the cells with the DNA on ice, followed by 2 minutes at 42° C., 5 minutes at room temp. The cells were allowed to recover for 1 hour at 37° C. in 3 ml of 2XYT medium. Small aliquots (50 µl) of the transformation reaction were plated on LB-plates containing ampicillin (100 µg/ml) and the plates were incubated overnight at 37° C.

b) Screening for Recombinant Plasmid Clones: Screening for the NLS8a Insert by Colony Lift and Hybridization In order to identify which colonies carried plasmids with the NLS insert, cells were screened using a colony lift and hybridization procedure. The DNA probe was prepared by labeling 202 pmol of NLS8a complement strand with 1 µl (0.015 mCi)[γ³²-P] ATP (NEN Life Science Products, Inc., Boston, Mass.). The 20 µl reaction contained 2 µl 10×T4 polynucleotide kinase reaction buffer (1×composition: 70 mM Tris-HCl pH 7.6, 10 mM MgCl$_2$, 5 mM dithiothreitol) (New England Biolabs, Beverly, Mass.), 1 μl (10 units) T4 polynucleotide kinase (New England BioLabs, Beverly, Mass.), and 15 μl ddH$_2$O. The kinase reaction was incubated at 37° C. for 1 hour. For colony lifts from the transformation plates described above, 541 paper disks (Whatman International Ltd., Maidstone, UK) were placed on top of the colonies on agar plates. The paper disk orientation with respect to the spatial arrangement of the cell colonies was marked with pinholes. The 541 filter disks were quickly lifted from the plates so that the cell colonies cleanly adhered to the paper. The plates were incubated at 37° C. for 2 days to re-grow the colonies. To break open the cells in preparation for hybridization, each 541 filter was placed colony side down on Whatman 3 mm paper, soaked in 0.5 M NaOH for 5 min in such a manner that the liquid barely immersed the paper disk. Each 541 filter disk was washed successively with 0.5 M Tris-Cl (pH 7.5) and for 2×SSC (0.3 M NaCl, 0.03 M Na-Citrate) 5 minutes each in such a manner that the liquid barely immersed the paper disk. The preceding steps lysed the cells and removed the cellular debris, while significant amounts of the plasmid DNA remained on the paper disk. The plasmid DNA was linked to the 541 filter disk using the UV Stratalinker 2400 (Stratagene, La Jolla, Calif.) for 1.5 minutes. The filters were soaked in 200 ml prehybridization solution (20% formamide, 5×SSPE, 5×Denhardt's reagent, 100 μg/ml fish milt DNA, and 0.1% sodium dodecyl sulfate) in a 500 ml beaker for 20 min at 55° C. Then the filter disks were removed, and 20 μl of the labeled probe was added to the prehybridization solution. The solution was mixed and the pre-hybridized 541 filters were individually dropped into the beaker and incubated overnight at 55° C. The filters were washed successively with 200 ml 2×SSPE in a 500 ml beaker for 20 minutes until no residual radioactivity in the liquid wash was detected. The washed filters were air dried and exposed to an autoradiographic film for 5 days. Several positive colonies were transferred by coring with sterile Pasteur pipettes to 10 ml liquid LB media supplemented with 100 μg/ml ampicillin. The cultures were incubated at 37° C. overnight in 250 ml flasks. Plasmid DNA was extracted from each 10 ml overnight culture using the Promega WIZARD PLASMID MINIPREP (Promega, Madison, Wis.). The plasmid DNA was eluted from the spin column in 100 μl water.

2. *E. coli* Expression Constructs for NLS8a-T4-pdg a) Construction of a T4-pdg Gene Containing a Nuclear Localization Sequence (NLS)

Figure 17:
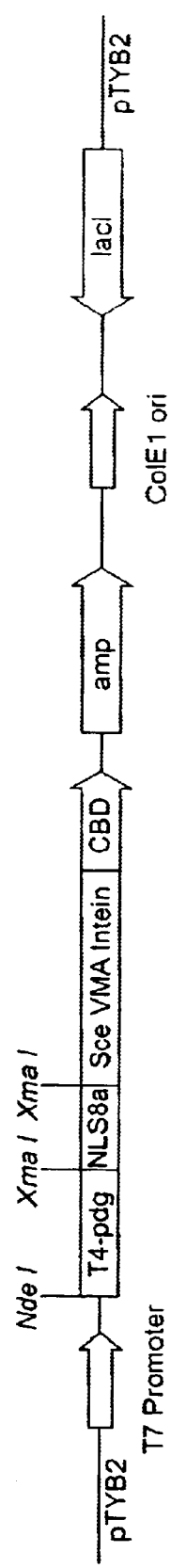
FIG. 17. Plasmid T4-pdg-NLS8a-pTYB2 (In frame fusion of T4-pdg, NLS8a, intein and chitin binding domain).

The T4-pdg gene was cloned into expression vector pTYB2 as previously described (Garvish and Lloyd, *J. Mol. Biol.*, 295, 479–488 (2000)) to generate plasmid T4-pdg-pTYB2 (FIG. 4). Cloning of the NLS8a to the XmaI site of T4-pdg-pTYB2 was performed exactly as described in 1a to generate plasmid NLS8a-T4-pdg-pTYB2 (FIG. 17).

b) Screening for Recombinant Plasmid Clones

Screening of recombinant clones containing the NLS8a insert was performed using colony lift hybridization as described above.

Figure 18:
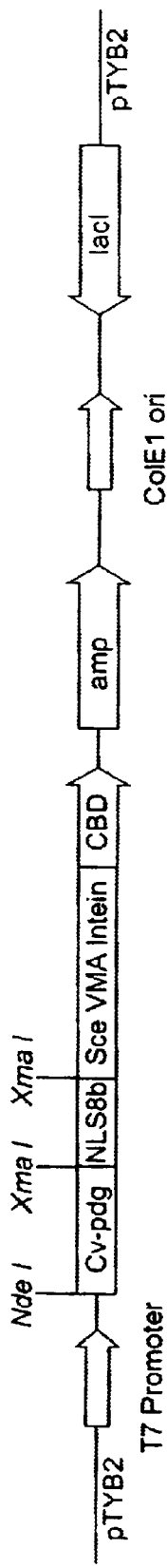
FIG. 18. Plasmid cv-pdg-NLS8b-pTYB2 (In frame fusion of cv-pdg, NLS8b, intein and chitin binding domain).

3. *E. coli* Expression Constructs for NLS8b-cv-pdg a) Cloning of NLS8b to cv-pdg Synthetic oligonucleotides were designed to encode codons for 8 amino acids PKKKRKRL (NLS8b) (SEQ ID NO:30) that are a functional equivalent to a NLS consensus sequence, retaining 6 basic amino acids in a row. These DNAs also contained sequences for cloning the NLS8b coding sequence into the XmaI site of the cv-pdg-pTYB2 plasmid (FIG. 18). As designed, this sequence contains a stop codon (TAG) that prevents production of cv-pdg pro-tein as a fusion with the downstream chitin binding domain if the NLS8b sequence is ligated in the reverse orientation. For the construction of the NLS8b, the following oligonucleotides were used: 5' CCGGGCCAAAGAAAAAGAG-GAAGAGGCTAC (SEQ ID NO:31), and 5'CCGGG TAGCCTCTTCCTCTTTTTCTTTGGC (SEQ ID NO:32). Each oligonucleotide was resuspended in water to a final concentration of 161 pmol/μl and 192 pmol/μl, respectively. The oligonucleotides were annealed and ligated into the XmaI site of the cv-pdg-pTYB2 plasmid as described above. 5 μl of each ligation reaction were used to transform CaCl$_2$ competent DH5α *E. coli* (200 μl) as above.

b) Screening for Recombinant Plasmid Clones

Screening of recombinant clones with the NLS8b insert was preformed using colony lift hybridization as described above.

Figure 19:
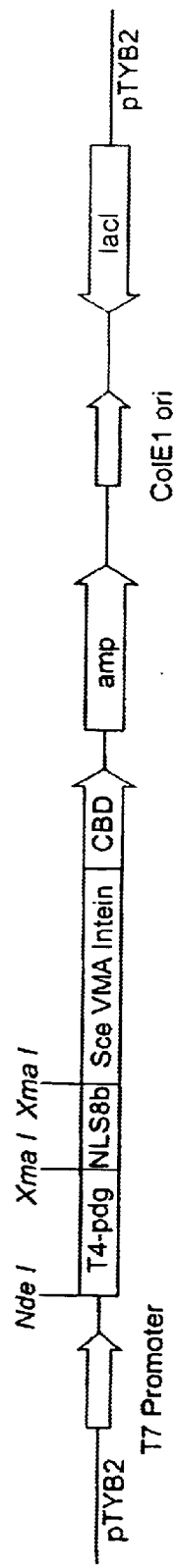
FIG. 19. Plasmid T4-pdg-NLS8B-pTYB2 (In frame fusion of T4-pdg, NLS8b, intein, and chitin binding domain).

4. *E. coli* Expression Constructs for NLS8b-T4-pdg a) Construction of a T4 pdg Gene Containing NLS8b Cloning of the NLS8b into T4-pdg-pTYB2 was performed as described above to generate plasmid T4-pdg-NLS8b-pTYB2 (FIG. 19).

b) Screening of Recombinant Plasmid Clones

Screening of recombinant clones with the NLS8b insert was preformed using colony lift hybridization as described above.

5. Protein Purification from *E. coli* a) Purification of T4-pdg-NLS8a

For large scale expression, 10 ng of T4-pdg-NLS8a-pTYB2 (FIG. 18) was used to transform the expression host *E. coli* ER2566 as described previously. A single colony was inoculated into 1 Liter LB supplemented with 100 μl ampicillin/liter and incubated with shaking overnight at 37° C. A 16-liter LB supplemented with 100 μl ampicillin/liter culture fermentation was inoculated with the 1 Liter overnight culture. The cells were grown at 37° C. (pH 7.0, constant) until the culture OD$_{600}$ reached 0.53. Cells were induced to express the T4-pdg-NLS8a with 0.3 mM IPTG. After a 6 hour induction at 25° C., cells were pelleted by centrifugation at 4° C. The 82 g cell pellet was resuspended in 600 ml Buffer A (50 mM Tris-HCl pH 8.0, 500 mM NaCl, 0.1 mM PMSF, 1 mM EDTA, and 0.1% Triton X-100. The cells were disrupted by sonication on ice for 900 total seconds. The sonicator was programmed to sonicate at 1 pulse per second for 30 seconds, with a 30-seconds pause between sonications. Cellular debris was pelleted by centrifugation at 33,000×g in a Beckman L-79 ultracentrifuge, type-19 rotor, and the supernatant retained.

The supernatant was loaded into a 50 mm diameter by 70 mm length XK column (Pharmacia, Piscataway, N.J.) filled with 100 ml chitin matrix (New England BioLabs, Beverly, Mass.) pre-equilibrated with Buffer B (20 mM Tris-HCl H 8.0, 500 mM NaCl, and 0.1 mM EDTA). The column was washed with 3 column volumes of Buffer B, followed by 1.3 column volumes of Buffer C (30 mM DTT, 20 mM Tris-HCl pH8.0, 500 mM NaCl, and 0.1 mM EDTA). Following an overnight incubation at 4° C. to facilitate the intein-mediated cleavage of T4-pdg-NLS8a from the 55 kDa intein-chitin binding domain (ICBD), the protein was eluted with Buffer D (20 mM Tris-HCl pH 8.0, 500 mM NaCl, and 0.1 mM EDTA.

b) Purification of NLS8b-T4-pdg

The purification of T4-pdg NLS8b was performed identically to that described in 5a except the cell pellet contained 70 grams of packed cells and they were resuspended in 400 ml Buffer A prior to sonication.

c) Purification of cv-pdg-NLS8a

The purification of cv-pdg-NLS8a was performed identically to that described in 5a except the weight of the starting packed cell mass was 100 grams.

d) Purification of NLS8b-cv-pdg

The purification of cv-pdg-NLS8b was performed as described in 5a.

6. Purity of Recombinant Enzymes

The final purity of T4-pdg-NLS8a and 8b and cv-pdg-NLS8a and 8b was determined by resolving the extracts on an SDS-polyacrylamide gel and stained with Coomassie blue. T4-pdg-NLS8a and 8b and cv-pdg-NLS8a and 8b were detected and determined to be >95% pure.

7. Activity of Recombinant Enzymes: Plasmid Nicking Assay a) Substrate Preparation: Introduction of Cyclobutane Pyrimidine Dimers (CPD) into pBR322 Plasmid.

pBR322 DNA (23 µg) was resuspended in 38 µl 10 mM Tris-HCl pH 7.5, 1 mM EDTA, resulting in a DNA concentration of 0.3 µg/µl. The plasmid DNA was Uv-irradiated for 5 min at 100 µW/cm$^2$ using a G15T8 germicidal lamp (peak wavelength at 254 nm). This step introduced 10 CPDs per plasmid molecule.

b) Nicking Reaction

A 402.5 µl reaction mastermix was made by combining 69 µl of UV-irradiated plasmid DNA, 46 µl 10×reaction buffer (250 mM sodium phosphate pH 6.8, 1.25 M NaCl, 10 mM EDTA), 4.6 µl of 10 mg/ml BSA, and 282.9 µl ddH$_2$O. The mastermix was allowed to equilibrate in a 20° C. water bath. Aliquots of the mastermix (17.5 µl) containing 1 µg UV-irradiated DNA were transferred into plastic eppendorf tubes. Stock enzymes were diluted 1:100, 1,000, 5,000 or 10,000 in 25 mM sodium phosphate (pH 6.8), 125 mM NaCl, 1 mM EDTA and 100 ug/ml BSA. A total of 2.5 µl of each enzyme dilution was added to the appropriately labeled tubes in the previous step. The 20 µl nicking reaction was incubated in a 20° C. water bath for 15 minutes. The reactions were stopped with 20 µl 20×stop buffer (50 mM Tris-HCl pH 8.0, 10 mM EDTA, 2% SDS, 40% sucrose, and 0.1 (weight/volume) bromophenol blue). A total of 20 µl of the stopped reaction was electrophoresed through a 0.7% agarose gel (2.8 grams Gibco BRL agarose in 400 ml 1×TBE) at 116 volts for 2.6 hours. This step separated the substrate (form I DNA) from the nicked products (forms II and III DNAs). The reaction products were visualized under UV light after staining with ethidium bromide 0.5 µg/ml in 1×TBE. T4-pdg-NLS8a and T4-pdg NLS8b nicked approximately 50% of the substrate at a 1:550 dilution. Cv-pdg-NLS8a and cv-pdgNLS8b nicked approximately 50% of the substrate at 1:1000 dilution. It was concluded that the NLS sequences do not alter enzyme activity.

2. Mammalian Expression a. Construction of cv-pdg-NLS8b-pEGFP-N3

Plasmid-cv-pdg-NLS8b pEGFP-N3 was constructed by inserting a DNA sequence encoding the NLS8b into the KpnI and BamHI sites of vector pEGFP-N3 (FIG. 12) (ClonTech). The DNA sequence encoding NLS8b-cv-pdg was PCR amplified using plasmid cv-pdg-NLS8b-pTYB2 (FIG. 18) as template. The primers used in amplifying the cv-pdg-NLS8b DNA fragment were designed to contain sequences for cloning into vector pEGFP-N3 and for optimal translation efficiency in mammalian cells. The sequences for the primers were as follows:

Each 50-µl PCR reaction consisted of 50 nanograms (ng) template, 125 ng each primer, 2.5 units Cloned Pfu TURBO DNA polymerase (Stratagene), 0.5 mM each dNTP (Stratagene), in 1×Cloned Pfu TURBO PCR buffer (20 mM Tris-HCl (pH 8.8), 20 mM MgSO$_4$, 10 mM KCl, 10 MM (NH$_4$)$_2$SO$_4$, 0.1% TritonX-100, and 0.1 mg/ml BSA). Prior to the addition of the DNA polymerase, the reaction mixture was subjected to an initial DNA denaturation at 95° C. for 10 min. The DNA polymerase was then added followed by 25 cycles of the following conditions: 96° C. DNA denaturation for 1 minute, 42° C., primer annealing for 1 minute, and 72° C. DNA polymerization for 2 minute. The PCR product was purified using QIAquick PCR Purification Kit (Qiagen) according to the manufacturer's protocol and eluted in 28 µl ddH$_2$O.

The purified DNA was then digested sequentially with 10 units of Kpn I for 1 hour at 37° C. and 16 units BamHI for 1 hour at 37° C. in a reaction containing appropriate buffers supplemented with BSA (0.1 mg/ml) as suggested by the enzyme supplier (New England BioLabs).

To prepare vector pEGFP-N3 for ligation, 7 µg was sequentially digested with Kpn I and BamHI using conditions as described for the PCR product digestion. The digested PCR fragment and plasmid vector were then purified as described. The purified digested vector DNA was treated with 0.1 unit CIAP (Gibco BRL) at 37° C. for 2 hours. The phosphatase was heat-inactivated at 87° C. for 20 minutes. The volume of the CIAP-treated plasmid was adjusted to 100 µl and purified by phenol extraction 120 µl phenol:choloroform:isoamyl alcohol (25:24:1, v/v) (Gibco BRL). Five µl of digested and purified PCR fragment and plasmid DNA were electrophoresed through 1% and 0.75% agarose gel (Gibco BRL), respectively. The DNA bands were visualized by ethidium bromide staining, and DNA concentrations were estimated based on band intensity. The estimated concentrations of the PCR fragment and vector plasmid were 600 µmole/µl and 0.16 mole/µl, respectively.

Figure 20:
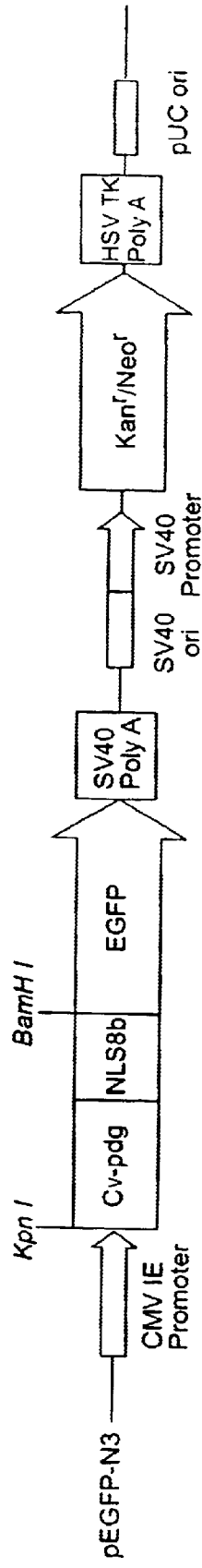
FIG. 20. Plasmid cv-pdg-NLS8b-pEGFP-N3 (In frame fusion of cv-pdg-NLS8b and EGFP).

The cv-pdg-NLS8b PCR-amplified insert was ligated to the vector plasmid at a 10:1 (insert:vector) molar ratio at 16° C. for 48 hours. The 30 µl ligation reaction consisted of 0.12 mole insert, 0.012 mole vector plasmid, 1600 units T4 Ligase (New England BioLabs), 7 mM ATP, and 1×T4 ligase buffer (50 mM Tris-HCl [pH 7.5], 10 mM dithiothreitol, 1 mM ATP, 25 µg/µl BSA). The 30 µl ligation reaction was used to transform E. coli DH5α as previously described, and 100 µl of the transformation reaction was plated on LB plates containing 30 µg/ml kanamycin. Plasmid DNAs from five kanamycin-resistant colonies were isolated using the WIZARD Plus SV Plasmid Mini Prep kit (Promega) as described by the manufacturer. The plasmid DNAs were linked to a nitrocellulose membrane for 1.5 minutes using the Stratalinker (Stratagene). The inserts were probed for by using [γ-P$^-$] ATP-labeled oligonucleotide (cv-pdg-NLS8b PCR reverse primer, SEQ ID NO:38. Two positive clones were confirmed to contain the cv-pdg-NLS8b between the Kpn I and Bam HI sites of the pEGFP-N3 plasmid by automated fluorescence DNA sequencing (FIG. 20).

5'ATACGG GGTACCACCATGACACGTGTGAATCTCG 3' (forward)    (SEQ ID NO: 35) and

5'TTTCGCGGATCCTAGCCTCCTCCTCCTTTTCTTTGG 3' (NLS8b reverse)   (SEQ ID NO: 36).

b. Construction of Plasmid cv-pdg-NLS8B-stop-pEGFP-N3

Figure 21:
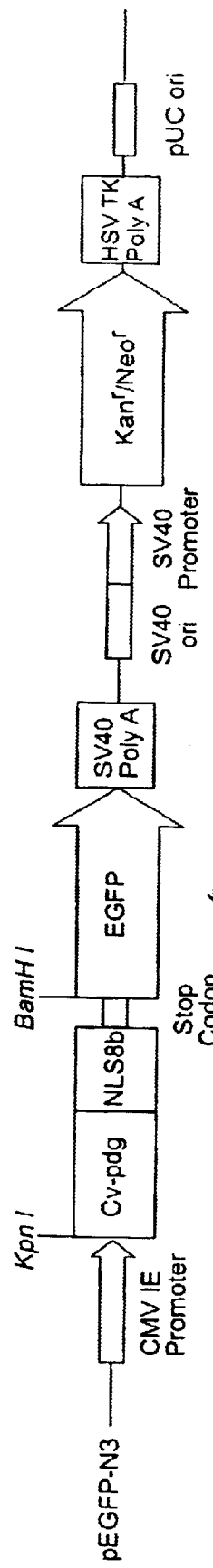
FIG. 21. Plasmid cv-pdg-NLS8b-x-pEGFP-N3 (In frame fusion of cv-pdg-NLS8b followed by a stop codon).

As designed, the product of cv-pdg-NLS8b is fused in-frame with EGFP. However, for certain studies, it is desirable that the cv-pdg-NLS8b protein be produced, not fused to EGFP at the C-terminus. To accomplish this a stop codon was introduced between the NLS8b coding region and the EGFP gene to yield cv-pdg-NLS8b*pEGFP-N3 (FIG. 21). The PCR-amplification, ligation, screening, and HeLa-S3 transfection processes were performed exactly in the same manner as was previously described for the construction of plasmid cv-pdg-NLS8b-pEGFP except that the reverse primer was as follows: 5' TTTCGCGGATCCTTAT-AGCCTCCTCCTCCTTTTCTTTGG 3' (SEQ ID NO:37).

c. Construction of T4-pdg-NLS8a-pEGFP-N3

Figure 22:
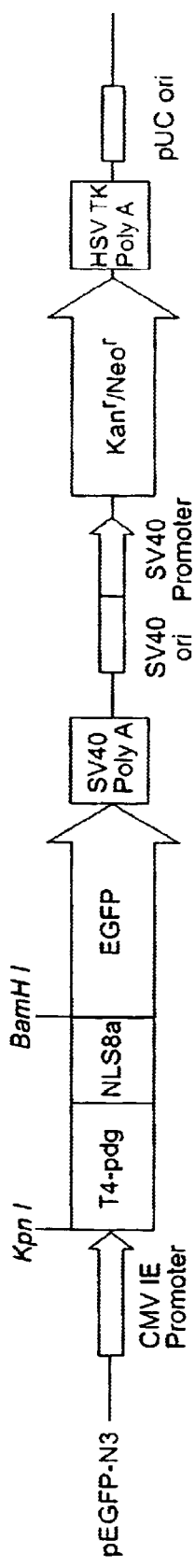
FIG. 22. Plasmid-T4-pdg-NLS8a-pEGFP-N3 (In frame fusion of T4-pdg-NLS8a and EGFP).

The DNA sequence encoding for the T4-pdg-NLS8a was PCR-amplified using plasmid T4-pdg-NLS8a-pTYB2 (FIG. 17) as template. The forward primer 5' GACGGGGTAC-CACCATGACTCGTATCAACCTTACTTTAGTATCTG 3' (SEQ ID NO:38) contained the Kpn I restriction sequence for inserting the PCR product into the vector plasmid and a consensus Kozak sequence for optimal translation efficiency in mammalian cells. The reverse primer was 5' TTTCGCG-GATCCTAGCCTCCTTTTCCTCTTCTTTGG 3' (SEQ ID NO:39). The construction was performed as previously described and yielded an in-frame fusion of T4-pdg-NLS8a and EGFP genes (FIG. 22).

d. Construction of Plasmid T4-pdg-NLS8a-stop-pEGFP-N3

Figure 23:
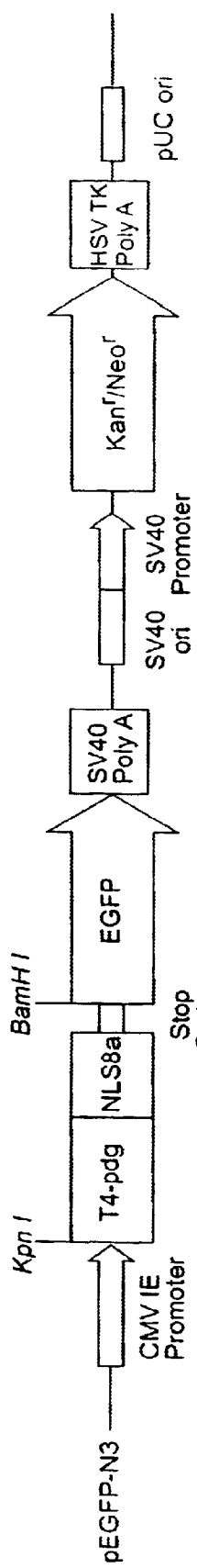
FIG. 23. Plasmid-T4-pdg-NLS8a-x-pEGFP-N3 (In frame fusion of T4-pdg-NLS8a followed by a stop codon).

The translation product of plasmid pEGFP-N3-T4-pdg-NLS8a is a complete fusion protein of T4-pdg-NLS8a and EGFP. However, to express only T4 pdg NLS8a in mammalian cells, a top codon must be added between the sequences encoding the NLS8a and EGFP. To accomplish this, PCR-amplification, ligation, screening, and HeLa-S3 transfection processes were performed exactly in the same manner as was previously described, except the reverse primer was 5' TTTCGCGGATCCTTATAGCCTCCTTTTC-CTCTTCTTTGG 3' (SEQ ID NO:40) (FIG. 23). This plasmid will express T4-pdg-NLS8a in mammalian cells.

e. Transfection of HeLa-S3 cells with T4-pdg-NLS8a-pEGFP-N3 for Biological Assays One plasmid clone (4 µg) of T4-pdg-NLS8a-pEGFP was used to transfect a human cell line HeLa-S3 using LipofectAMINE PLUS Reagent (GibcoBRL) according to the manufacturer's suggested protocol. The HeLa-S3 cells were obtained from American Type Culture Collection and were maintained in high-glucose Dulbeco's Modified Eagle Media (DMEM) (GibcoBRL) supplemented with 10% fetal bovine serum (GibcoBRL), 2 mM L-glutamine (GibcoBRL), 0.01 mM Hepes, 1×Gibco's antibiotic/antimycotic solution (100 units/ml penicillin G sodium, 100 µg/ml streptomycin sulfate, 0.25 µg/ml amphotericin B). Stable transfectants were established by adding a selective reagent G148 (0.4 mg/ml) (Geniticin, Mediatech, Herndon, Va.) to the growth medium at 48 h post-transfection. After 10 days, the transfected cells were maintained in 12 ml growth medium containing 2 mg/ml G148. The cells were grown in a humidified atmosphere with 5% $CO_2$ at 37° C.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Sequence Listing Free Text

SEQ ID NOs:1, 27, 30, and 47 Amino acid sequence
SEQ ID NOs:2–26, 28, 29, 31–40, 48, and 49 Oligonucleotide primer

What is claimed is:

1. An isolated polypeptide comprising:
   an amino acid sequence selected from the group consisting of SEQ ID NO:41, SEQ ID NO:42, and SEQ ID NO:43; and
   a nuclear or mitochondrial targeting sequence.

2. A method for increasing the repair rate of damaged bases in a cell, the method comprising introducing to a cell exposed to or at risk of exposure to an agent that damages DNA a composition comprising an amount of an isolated polypeptide effective to increase the repair rate of damaged DNA in the cell compared to a cell that does not comprise the polypeptide, wherein the polypeptide comprises an amino acid sequence selected from the group consisting of SEQ ID NO: 41, SEQ ID NO: 42, and SEQ ID NO:43, and wherein the polypeptide further comprises a nuclear or mitochondrial targeting sequence.

3. A method for treating mutagenesis in a subject, the method comprising introducing to a subject exposed to or at risk of exposure to an agent that damages DNA a composition comprising an effective amount of an isolated polypeptide, wherein the polypeptide comprises an amino acid sequence selected from the group consisting of SEQ ID NO:41, SEQ ID NO:42, and SEQ ID NO:43, and wherein the polypeptide further comprises a nuclear or mitochondrial targeting sequence.

4. A method for treating immunosuppression in a subject, the method comprising introducing to a subject exposed to or at risk of exposure to an agent that damages DNA a composition comprising an effective amount of an isolated polypeptide, wherein the polypeptide comprises an amino acid sequence selected from the group consisting of SEQ ID NO:41, SEQ ID NO:42, and SEQ ID NO:43, and wherein the polypeptide further comprises a nuclear or mitochondrial targeting sequence.

5. A method for treating tumor formation in a subject, the method comprising introducing to a subject exposed to or at risk of exposure to an agent that damages DNA a composition comprising an effective amount of an isolated polypeptide, wherein the polypeptide comprises an amino acid sequence selected from the group consisting of SEQ ID NO:41, SEQ ID NO:42, and SEQ ID NO:43, and wherein the polypeptide further comprises a nuclear or mitochondrial targeting sequence.

6. A method for treating apoptotic cell formation in a subject, the method comprising introducing to a subject exposed to or at risk of exposure to an agent that damages DNA a composition comprising an effective amount of an isolated polypeptide, wherein the polypeptide comprises an amino acid sequence selected from the group consisting of SEQ ID NO:41, SEQ ID NO:42, and SEQ ID NO:43, and wherein the polypeptide further comprises a nuclear or mitochondrial targeting sequence.

7. A composition comprising the polypeptide of claim 1 and a pharmaceutically acceptable carrier.

* * * * *

SEQUENCE LISTING

```
<160> NUMBER OF SEQ ID NOS: 49

<210> SEQ ID NO 1
<211> LENGTH: 18
<212> TYPE: PRT
<213> ORGANISM: Artificial Sequence
<220> FEATURE:
<223> OTHER INFORMATION: A mitochondrial localization sequence

<400> SEQUENCE: 1

Met Ala Leu His Ser Met Arg Lys Ala Arg Glu Arg Trp Ser Phe Ile
1               5                   10                  15

Arg Ala

<210> SEQ ID NO 2
<211> LENGTH: 55
<212> TYPE: DNA
<213> ORGANISM: Artificial Sequence
<220> FEATURE:
<223> OTHER INFORMATION: Oligonucleotide primer

<400> SEQUENCE: 2
tatggcgtta catagcatgc gcaaagcgcg cgaacgctgg agctttatta gagca         55
```

```
<210> SEQ ID NO 3
<211> LENGTH: 55
<212> TYPE: DNA
<213> ORGANISM: Artificial Sequence
<220> FEATURE:
<223> OTHER INFORMATION: Oligonucleotide primer

<400> SEQUENCE: 3
tatgctctaa taaagctcca gcgttcgcgc gctttgcgca tgctgtataa cgcca          55

<210> SEQ ID NO 4
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 4
atacggggta ccaccatggc gttacatagc atgcg                                35

<210> SEQ ID NO 5
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 5
gcacgcggat ccttaattat tgctggtttt agctttcg                             38

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 6
gctttattag agcaacacgt gtgaatc                                         27

<210> SEQ ID NO 7
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 7
gattcacacg tgttgctcta ataaagc                                         27

<210> SEQ ID NO 8
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 8
atacggggta ccaccatggc gttacatagc atgcg                                35

<210> SEQ ID NO 9
<211> LENGTH: 34
<212> TYPE: DNA
<213> ORGANISM: Artificial Sequence
<220> FEATURE:
<223> OTHER INFORMATION: Oligonucleotide primer
```

```
<400> SEQUENCE: 9
gcacgcggat ccttatgcat aaatcgcctt accg                          34

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 10
gctttattag agcaactcgt atcaacc                                  27

<210> SEQ ID NO 11
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 11
ggttgatacg agttgctcta ataaac                                   26

<210> SEQ ID NO 12
<211> LENGTH: 106
<212> TYPE: DNA
<213> ORGANISM: Artificial Sequence
<220> FEATURE:
<223> OTHER INFORMATION: Oligonucleotide primer

<400> SEQUENCE: 12
tatgggcgtg ttttgcttag gcccgtgggg cttaggccgc aaattacgca ccccgggcaa    60
aggcccgtta cagttattat cgcgcttatg cggcgatcat ttacag                  106

<210> SEQ ID NO 13
<211> LENGTH: 105
<212> TYPE: DNA
<213> ORGANISM: Artificial Sequence
<220> FEATURE:
<223> OTHER INFORMATION: Oligonucleotide primer

<400> SEQUENCE: 13
tactgtaaat gatcgccgca taagcgcgat aataactgta acgggccttt gcccggggtg    60
cgtaatttgc ggcctaagcc ccacgggcct aagcaaacac gccca                   105

<210> SEQ ID NO 14
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 14
atacggggta ccaccatggg cgtgttttgc ttagg                         35

<210> SEQ ID NO 15
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 15
gcacgcggat ccttaattat tgctggtttt agctttcg                      38
```

<210> SEQ ID NO 16
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 16
ggcgatcatt tacagactcg agtgaatctc gtaccg                          36

<210> SEQ ID NO 17
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 17
cggtacgaga ttcactcgag tctgtaaatg atcgcc                          36

<210> SEQ ID NO 18
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 18
atacggggta ccaccatggg cgtgttttgc ttagg                           35

<210> SEQ ID NO 19
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 19
gcacgcggat ccttatgcat aaatcgcctt accg                            34

<210> SEQ ID NO 20
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 20
ggcgatcatt tacagactcg tatcaacctt ac                              32

<210> SEQ ID NO 21
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 21
gtaaggttga tacgagtctg taaatgatcg cc                              32

<210> SEQ ID NO 22
<211> LENGTH: 34
<212> TYPE: DNA
<213> ORGANISM: Artificial Sequence
<220> FEATURE:

```
<223> OTHER INFORMATION: Oligonucleotide primer

<400> SEQUENCE: 22
atacggggtc caccatggcg ttacatagca tgcg                          34

<210> SEQ ID NO 23
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 23
gcacgcggat ccttaattat tgctggtttt agctttcg                      38

<210> SEQ ID NO 24
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 24
atacggggta ccaccatgac acgtgtgaat ctcg                          34

<210> SEQ ID NO 25
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 25
gcacgcggat cctaatgcat aaatcgcctt accg                          34

<210> SEQ ID NO 26
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 26
gacggggtac caccatgact cgtatcaacc ttactttagt atctg               45

<210> SEQ ID NO 27
<211> LENGTH: 8
<212> TYPE: PRT
<213> ORGANISM: Artificial Sequence
<220> FEATURE:
<223> OTHER INFORMATION: A consensus nuclear localization sequence

<400> SEQUENCE: 27

Pro Lys Lys Arg Lys Arg Arg Leu
1               5

<210> SEQ ID NO 28
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 28
ccgggccaaa gaagaggaaa aggaggctac                               30
```

<210> SEQ ID NO 29
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 29
ccgggtagcc tccttttcct cttctttggc          30

<210> SEQ ID NO 30
<211> LENGTH: 8
<212> TYPE: PRT
<213> ORGANISM: Artificial Sequence
<220> FEATURE:
<223> OTHER INFORMATION: A consensus nuclear localization sequence

<400> SEQUENCE: 30

Pro Lys Lys Lys Arg Lys Arg Leu
1               5

<210> SEQ ID NO 31
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 31
ccgggccaaa gaaaagagg aagaggctac          30

<210> SEQ ID NO 32
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 32
ccgggtagcc tcttcctctt tttctttggc          30

<210> SEQ ID NO 33
<211> LENGTH: 54
<212> TYPE: DNA
<213> ORGANISM: Artificial Sequence
<220> FEATURE:
<223> OTHER INFORMATION: Nucleotides encoding a mitochondrial
      localization sequence

<400> SEQUENCE: 33
atggcgttac atagcatgcg caaagcgcgc gaacgctgga gctttattag agca          54

<210> SEQ ID NO 34
<211> LENGTH: 105
<212> TYPE: DNA
<213> ORGANISM: Artificial Sequence
<220> FEATURE:
<223> OTHER INFORMATION: Nucleotides encoding a mitochondrial
      localization sequence

<400> SEQUENCE: 34
atgggcgtgt tttgcttagg cccgtgggc ttaggccgca aattacgcac cccgggcaaa     60
ggcccgttac agttattatc gcgcttatgc ggcgatcatt tacag                   105

<210> SEQ ID NO 35

```
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 35
atacggggta ccaccatgac acgtgtgaat ctcg                           34

<210> SEQ ID NO 36
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 36
tttcgcggat cctagcctcc tcctcctttt ctttgg                         36

<210> SEQ ID NO 37
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 37
tttcgcggat ccttatagcc tcctcctcct tttctttgg                      39

<210> SEQ ID NO 38
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 38
gacggggtac caccatgact cgtatcaacc ttactttagt atctg                45

<210> SEQ ID NO 39
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 39
tttcgcggat cctagcctcc ttttcctctt ctttgg                         36

<210> SEQ ID NO 40
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 40
tttcgcggat ccttatagcc tccttttcct cttctttgg                      39

<210> SEQ ID NO 41
<211> LENGTH: 141
<212> TYPE: PRT
<213> ORGANISM: Chlorella virus

<400> SEQUENCE: 41

Met Thr Arg Val Asn Leu Val Pro Val Gln Glu Leu Ala Asp Gln His
```

-continued

```
              1               5                  10                 15
          Leu Met Ala Glu Phe Arg Glu Leu Lys Met Ile Pro Lys Ala Leu Ala
                           20                  25                  30

Arg Ser Leu Arg Thr Gln Ser Ser Glu Lys Ile Leu Lys Lys Ile Pro
                       35                  40                  45

Ser Lys Phe Thr Leu Asn Thr Gly His Val Leu Phe Phe Tyr Asp Lys
               50                  55                  60

Gly Lys Tyr Leu Gln Gln Arg Tyr Asp Glu Ile Val Val Glu Leu Val
           65                  70                  75                  80

Asp Arg Gly Tyr Lys Ile Asn Val Asp Ala Lys Leu Asp Pro Asp Asn
                           85                  90                  95

Val Met Thr Gly Glu Trp Tyr Asn Asp Tyr Thr Pro Thr Glu Asp Ala
                       100                 105                 110

Phe Asn Ile Ile Arg Ala Arg Ile Ala Glu Lys Ile Ala Met Lys Pro
                   115                 120                 125

Ser Phe Tyr Arg Phe Thr Lys Ala Lys Thr Ser Asn Asn
               130                 135                 140
```

<210> SEQ ID NO 42
<211> LENGTH: 138
<212> TYPE: PRT
<213> ORGANISM: Bacteriophage T4

<400> SEQUENCE: 42

```
          Met Thr Arg Ile Asn Leu Thr Leu Val Ser Glu Leu Ala Asp Gln His
           1               5                  10                 15

Leu Met Ala Glu Tyr Arg Glu Leu Pro Arg Val Phe Gly Ala Val Arg
                           20                  25                  30

Lys His Val Ala Asn Gly Lys Arg Val Arg Asp Phe Lys Ile Ser Pro
                       35                  40                  45

Thr Phe Ile Leu Gly Ala Gly His Val Thr Phe Phe Tyr Asp Lys Leu
               50                  55                  60

Glu Phe Leu Arg Lys Arg Gln Ile Glu Leu Ile Ala Glu Cys Leu Lys
           65                  70                  75                  80

Arg Gly Phe Asn Ile Lys Asp Thr Thr Val Gln Asp Ile Ser Asp Ile
                           85                  90                  95

Pro Gln Glu Phe Arg Gly Asp Tyr Ile Pro His Glu Ala Ser Ile Ala
                       100                 105                 110

Ile Ser Gln Ala Arg Leu Asp Glu Lys Ile Ala Gln Arg Pro Thr Trp
                   115                 120                 125

Tyr Lys Tyr Tyr Gly Lys Ala Ile Tyr Ala
               130                 135
```

<210> SEQ ID NO 43
<211> LENGTH: 268
<212> TYPE: PRT
<213> ORGANISM: Micrococcus luteus

<400> SEQUENCE: 43

```
          Met Glu Thr Glu Ser Thr Gly Thr Pro Thr Gly Glu Thr Arg Leu Ala
           1               5                  10                 15

Leu Val Arg Arg Ala Arg Arg Ile Asp Arg Ile Leu Ala Glu Thr Tyr
                           20                  25                  30

Pro Tyr Ala Val Ala Glu Leu Asp Phe Glu Thr Pro Phe Glu Leu Leu
                       35                  40                  45

Val Ala Thr Val Leu Ser Ala Gln Thr Thr Asp Val Arg Val Asn Ala
```

```
              50                  55                  60
Ala Thr Pro Ala Leu Phe Ala Arg Phe Pro Asp Ala His Ala Met Ala
 65                  70                  75                  80

Ala Ala Thr Glu Pro Glu Leu Gln Glu Leu Val Arg Ser Thr Gly Phe
                 85                  90                  95

Tyr Arg Asn Lys Ala Ser Ala Ile Leu Arg Leu Ser Gln Glu Leu Val
            100                 105                 110

Gly Arg His Asp Gly Glu Val Pro Ala Arg Leu Glu Asp Leu Val Ala
            115                 120                 125

Leu Pro Gly Val Gly Arg Lys Thr Ala Phe Val Val Leu Gly Asn Ala
        130                 135                 140

Phe Gly Gln Pro Gly Ile Thr Val Asp Thr His Phe Gly Arg Leu Ala
145                 150                 155                 160

Arg Arg Leu Gly Phe Thr Asp Glu Thr Asp Pro Gly Lys Gly Arg Ala
                165                 170                 175

Arg Arg Gly Arg Pro Val Pro Pro Ala Arg Asp Trp Thr Met Leu Ser
            180                 185                 190

His Arg Leu Ile Phe His Gly Arg Arg Val Cys His Ala Arg Arg Pro
        195                 200                 205

Ala Cys Gly Arg Cys Pro Ile Ala Arg Trp Cys Pro Ser Tyr Ala Ala
    210                 215                 220

Gly Glu Thr Asp Pro Glu Arg Ala Arg Ala Leu Leu Ala Tyr Glu Leu
225                 230                 235                 240

Lys Pro Gly Arg Glu Glu Leu Leu Glu Leu Leu Arg Ala Gly Arg Thr
                245                 250                 255

Ala Gly Ala Ala Gly Pro Arg Pro Arg Ala Gly Gly
            260                 265

<210> SEQ ID NO 44
<211> LENGTH: 426
<212> TYPE: DNA
<213> ORGANISM: Chlorella virus

<400> SEQUENCE: 44
atgacacgtg tgaatctcgt accggttcaa gaattagctg accagcatct catggcagaa      60
tttcgtgaac ttaagatgat tccgaaggca ctcgcaagaa gtcttcgaac tcaatcgtcc     120
gaaaaaatat tgaagaagat cccatcaaaa tttactctga acactggtca tgttctgttc     180
ttttacgata aaggcaagta tttgcaacaa cgatacgacg aaattgtcgt tgaacttgtt     240 gataggggt ataagataaa cgttgacgct aaactcgacc ctgataacgt gatgacggga      300
gagtggtaca atgattacac cccaacagaa gatgcgttta atattattcg agcgaggatt     360
gccgaaaaaa tcgctatgaa gccaagtttt tacaggttca cgaaagctaa accagcaat      420 aattaa                                                                426

<210> SEQ ID NO 45
<211> LENGTH: 417
<212> TYPE: DNA
<213> ORGANISM: Bacteriophage T4

<400> SEQUENCE: 45
atgactcgta tcaaccttac tttagtatct gaattggctg accaacactt aatggctgaa      60
tatcgtgaat tgccgcgtgt ttttggtgca gttcgtaagc atgttgctaa cggtaaacgt     120
gttcgtgatt ttaaaatcag tcctactttt atccttggcg caggtcatgt tacattcttt     180
```

```
tacgataagc tcgagttctt acgtaaacgt caaattgagc ttatagctga atgtttaaaa        240
cgtggtttta atatcaagga tactacagtc caggatatta gtgatattcc tcaggaattc        300
cgtggtgatt atattcccca tgaagcttct attgctatat cacaagctcg tttagatgaa        360
aaaattgcac aacgtcctac ttggtacaaa tactacggta aggcgattta tgcataa           417
```

<210> SEQ ID NO 46
<211> LENGTH: 968
<212> TYPE: DNA
<213> ORGANISM: Micrococcus luteus

<400> SEQUENCE: 46

```
atgcgcccgg aagcggggc cggacccggt gtggacgtcg catgcgcccc gctccctagg         60
atggtcggac ctgagcggat cgcacgaggg cgggaggaca cgcggatgga gacggagtcg        120
acgggcacgc cgaccgggga gacccggctg gccctggtgc gccgggcgcg gcggatcgac        180
cggatcctgg ccgagacgta cccgtacgcc gtcgccgagc tggacttcga gacgccgttc        240
gagctgctcg tggccacggt gctgtccgcc cagaccaccg acgtgcgggt caacgcagcc        300
acgccggcgc tgttcgcccg cttcccggat gcccacgcga tggccgcggc caccgagccc        360
gagctgcagg agctcgtgcg ctccacgggg ttctaccgga acaaggcctc cgcgatcctg        420
cggctgtccc aggagctcgt gggccggcac gacggcgagg tccccgcccg tctcgaggac        480
ctcgtggcgc tgcccggggt gggccgcaag accgcgttcg tggtgctcgg caacgccttc        540
ggccagcccg ggatcaccgt ggacacgcac ttcgccggc tcgcccggcg cctgggttc         600 acggacgaga ccgacccggg taaaggtcga gcacgccgtg gcgcccctgt tcccccccgcc       660 cgggactgga cgatgctctc ccaccggctg atcttccacg gccgccgcgt gtgccacgcg        720
cgccgcccgg cgtgcgggcg gtgcccgatc gcccgctggt gccgtcctca gccgcggggg       780
gagaccgacc ccgagcgggc gcgcgccctg ctggcctacg agctcaagcc cggccgggag        840
gagctgctcg agctcctgcg cgcggggcgg acggcgggag ctgcggggcc tcggccacgg        900
gctggaggct gagcgcccgg cctgcccgct cagccttttc ggtgagaccc gcgagatcgc        960
gaccgccg                                                                968
```

<210> SEQ ID NO 47
<211> LENGTH: 35
<212> TYPE: PRT
<213> ORGANISM: Artificial Sequence
<220> FEATURE:
<223> OTHER INFORMATION: A mitochondrial localization sequence

<400> SEQUENCE: 47

```
Met Gly Val Phe Cys Leu Gly Phe Trp Gly Leu Gly Arg Lys Leu Arg
1               5                  10                  15

Thr Phe Gly Lys Gly Pro Lys Gln Leu Leu Ser Arg Leu Cys Gly Asp
            20                  25                  30

His Leu Gln
        35
```

<210> SEQ ID NO 48
<211> LENGTH: 24
<212> TYPE: DNA
<213> ORGANISM: Artificial Sequence
<220> FEATURE:
<223> OTHER INFORMATION: Nucleotides encoding a nuclear localization
      sequence

<400> SEQUENCE: 48

-continued

```
ccaaagaaga ggaaaaggag gcta                                              24

<210> SEQ ID NO 49
<211> LENGTH: 24
<212> TYPE: DNA
<213> ORGANISM: Artificial Sequence
<220> FEATURE:
<223> OTHER INFORMATION: Nucleotides encoding a nuclear localization
      sequence

<400> SEQUENCE: 49
ccaaagaaaa agaggaagag gcta                                              24
```